(12) United States Patent
Vita et al.

(10) Patent No.: US 8,354,498 B2
(45) Date of Patent: Jan. 15, 2013

(54) CD4 MIMIC PEPTIDES AND THEIR USES

(75) Inventors: Claudio Vita, Gif-sur-Yvette (FR); Mireille Sauvage-Vita, legal representative, Gif-sur-Yvette (FR); Fabio Vita, legal representative, Gif-sur-Yvette (FR); Elena Vita, legal representative, Gif-sur-Yvette (FR); Loïc Martin, Gif-sur-Yvette (FR); François Stricher, Sant Cugat Del Valles (ES); Anne Descours, Montrouge (FR); Laurence Morellato, Cachan (FR)

(73) Assignee: Commissariat a l'Energie Atomique, Paris (FR)

( * ) Notice: Subject to any disclaimer, the term of this patent is extended or adjusted under 35 U.S.C. 154(b) by 717 days.

(21) Appl. No.: 12/304,485

(22) PCT Filed: May 9, 2007

(86) PCT No.: PCT/IB2007/002686
§ 371 (c)(1),
(2), (4) Date: Jun. 25, 2009

(87) PCT Pub. No.: WO2008/010088
PCT Pub. Date: Jan. 24, 2008

(65) Prior Publication Data
US 2009/0285798 A1 Nov. 19, 2009

(30) Foreign Application Priority Data
Jun. 13, 2006 (WO) .................. PCT/IB2006/002332

(51) Int. Cl.
*C07K 14/73* (2006.01)
(52) U.S. Cl. .................. 530/324; 530/403; 514/3.7
(58) Field of Classification Search .................. 530/324, 530/403; 514/3.7
See application file for complete search history.

(56) References Cited

U.S. PATENT DOCUMENTS
2005/0176642 A1 8/2005 Wang

FOREIGN PATENT DOCUMENTS
| WO | WO 02/059146 | 8/2002 |
| WO | WO 03/089000 | 10/2003 |
| WO | WO 2005/003296 | 1/2005 |

OTHER PUBLICATIONS

International Search Report and Written Opinion for PCT/IB2007/002686 filed May 5, 2007.
Martin L et al: "Rational design of a CD4 mimic that inhibits HIV-1 entry and exposes cryptic neutralization epitopes"; Nature Biotechnology, Nature Publishing Group, New York, NY, US; vol. 21, No. 1; Jan. 2003; pp. 71-76; XP001156366.
Huang C C et al: "Scorpion-Toxin Mimics in DC4 in Complex with Human Immunodeficiency Virus gp120"; Structure, Current Biology Ltd., Philadelphia, PA, US; vol. 13, No. 5; May 2005; pp. 755-768; XP004910457.
Stricher F et al: "A high-throughput flurorescence polarization assay specific to the CD4 binding site of HIV-1 glycoproteins based on a fluorescein-labelled CD4 mimic"; Biochemical Journal; vol. 390; 2005; pp. 29-39; XP002419847.
Hewer R & Meyer D: "Peptide immunogens based on the envelope region of HIV-1 are recognized by HIV/AIDS patients polyclonal antibodies and induce strong humoral immune responses in mice an rabbits"; Molecular Immunology; vol. 40, No. 6; Oct. 2003; pp. 327-335; XP002419839.

*Primary Examiner* — David Lukton
(74) *Attorney, Agent, or Firm* — Alston and Bird LLP

(57) ABSTRACT

An isolated peptide comprising the sequence (I): TPA-Asn-Leu-His-Phe-Cys-Gln-Leu-Xaa$^a$-Cys-Lys-Ser-Leu-Gly-Leu-Leu-Gly-Arg-Cys-Xaa$^b$-Xaa$^c$-Xaa$^d$-Xaa$^e$-Cys-Ala-Cys-Val-NH$_2$, wherein: TPA represents thiopropionic acid; Xaa$^a$ represents Arg, Lys; Xaa$^b$ represents Ala, Arg; Xaa$^c$ represents a D-amino acid; Xaa$^d$ represents Thr, Ser, Asn; Xaa$^e$ represents phenylalanine or a phenylalanine derivative having the structure (II), where A is absent or represents S, O, NH or CH$_2$, B is absent or represents a C$_1$ to C$_6$ branched or straight-chain alkyl, and R represents a C$_3$ to C$_6$ alkyl, heteroalkyl, cycloalkyl, heterocycloalkyl, cycloalkenyl, cycloheterocyloalkenyl, aryl, or heteroaryl, and the use of the peptide for manufacturing anti-HIV therapeutic or vaccine compositions are disclosed herein.

28 Claims, 19 Drawing Sheets

Deconvolution strategy

Synthesize 19 sublibrairies. Introduce each of the 19 possible (L)-aa at position 18 with a mixture of 19 (L)-aa x 34 x 34 (L).(D)-aa at positions 20, 21 and 22, respectively (21 964 theoritical peptides).

Proceed to A,B,C&D

Fix optimal residue at position 18, and prepare 19 sublibraries with position 20 occupied by one fixed (L)-aa and introduce a mixture of 34 x 34 (L).(D)-aa at positions 21 and 22 (1156 theorical peptides).

Proceed to A,B,C&D

Fix optimal residues at position 18 and 20, and prepare 34 sublibraries with position 21 occupied by one fixed (L).(D)-aa and introduce a mixture of 34 (L).(D)-aa at position 22 (34 therorical peptides).

Proceed to A,B,C&D

Fix optimal residues at position 18, 20 and 21, and prepare 34 peptides with position 22 occupied by one fixed (L).(D)-aa (34 pure peptide).

Procedure for sublibrary synthesis

A : Synthesis of sublibraries

B : Cleavage of the resin-bound sublibraries Folding and desalting by RP-HPLC

C : Global conformity of each sublibrary

Quantitative aa composition + CD + MS : if not conformed return to A

D: Biological Screening (ELISA and fluorescent polarization) to select otimal residue at selected position.

FIGURE 2

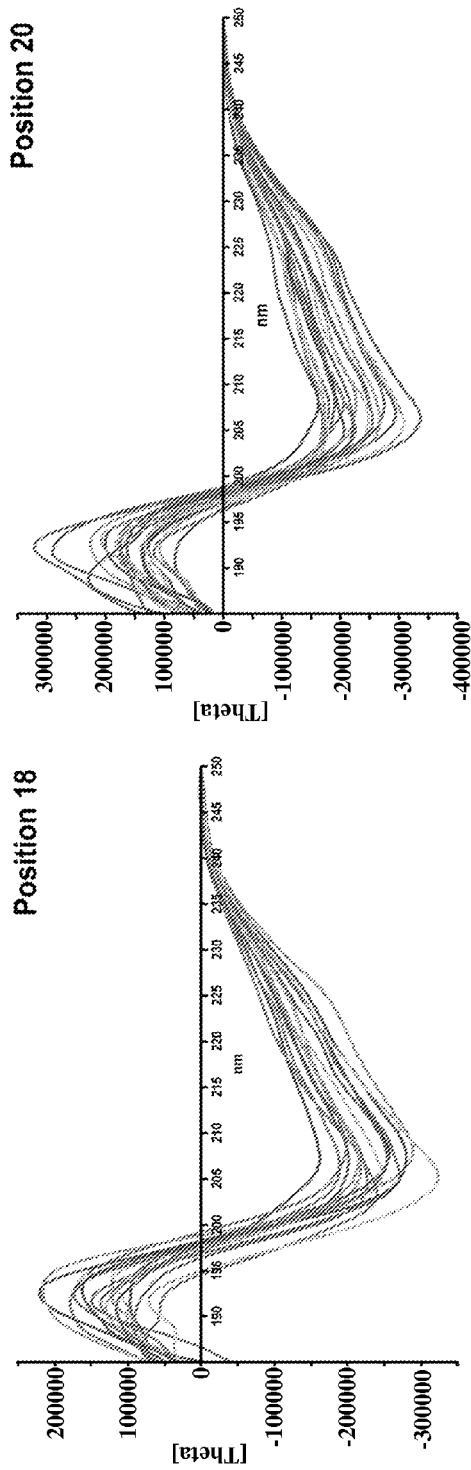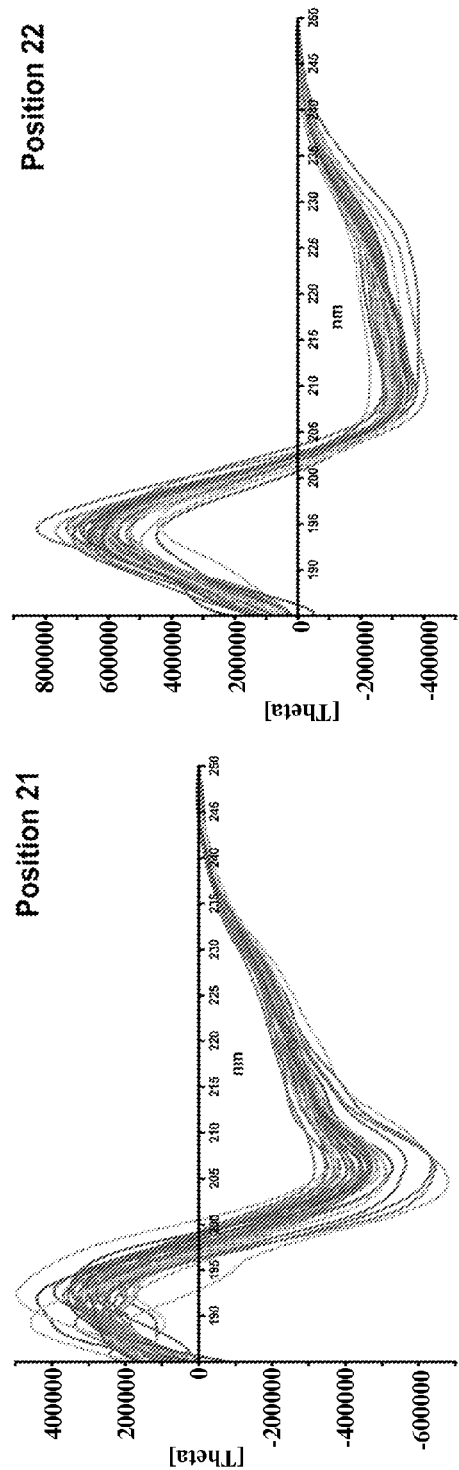
FIGURE 3

A
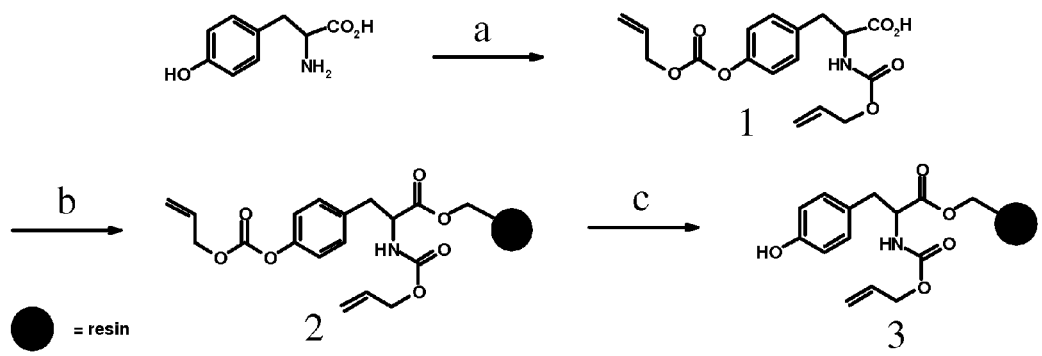
Conditions: (a) 3 equiv 4 M NaOH, 2 equiv allylchloroformate;
(b) 0.33 equiv Wang resin, 1 equiv DIC, 0.33 equiv DMAP, DMF;
(c) 20% piperidine in DMF
B
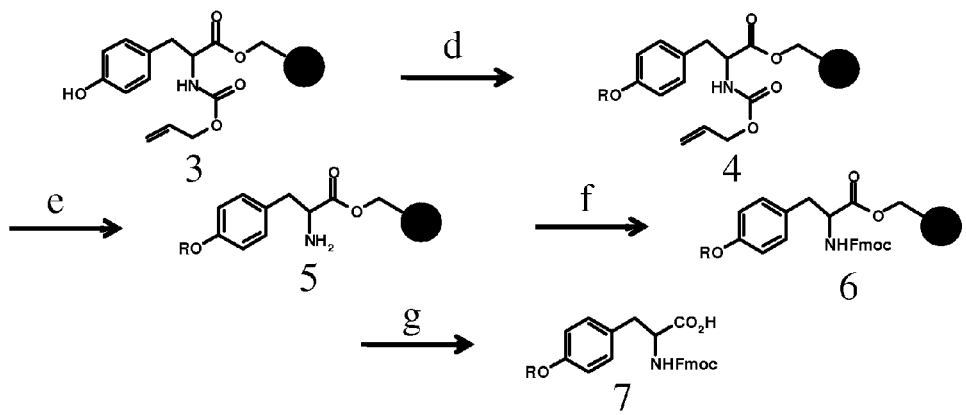
Conditions: (d) 5 equiv alcohol, PPh$_3$ and DIAD, THF, 1:1, 2x 24h;
(e) 0.5 equiv Pd(PPh$_3$)$_4$, THF:DMSO:0.5M HCl:morpholine (20:20:10:1);
(f) 3 equiv FmocCl, 4 equiv DIEA, DCM;
(g) TFA:DCM, 3:7, 1h
FIGURE 11

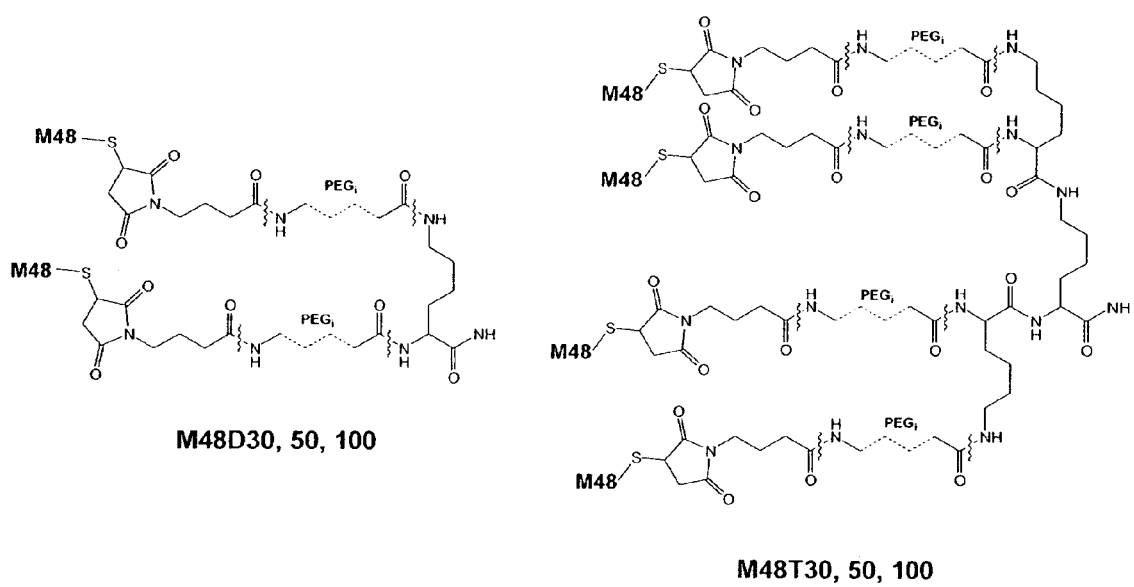
M48D30, 50, 100
M48T30, 50, 100
Where:
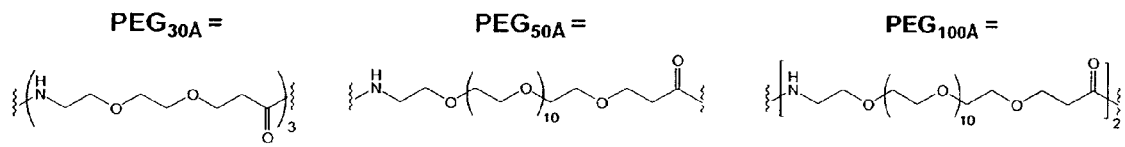
FIGURE 15

CD4 MIMIC PEPTIDES AND THEIR USES

CROSS REFERENCE TO RELATED APPLICATIONS

This application is a national stage application filed under 35 U.S.C. 371 of International Application No. PCT/IB2007/002686, filed May 9, 2007, which claims priority from International Application No. PCT/IB2006/002332, filed Jun. 13, 2006.

FIELD AND BACKGROUND OF THE INVENTION

The invention relates to optimized CD4 mimic peptides derived from the CD4M33 peptide (Martin et al., Nat. Biotechnol., 2003, 21, 71-76 and International PCT Application WO 02/059146) and to the use of these peptides for the manufacture of new anti-HIV medicines and vaccines.

The human immunodeficiency virus (HIV) has been implicated as the primary cause of the slowly degenerative immune system disease termed acquired immune deficiency syndrome (AIDS). In humans, HIV replication occurs prominently in CD4 T lymphocyte populations, and HIV infection leads to depletion of this cell type and eventually to immune incompetence, opportunistic infections, neurological dysfunctions, neoplastic growth, and ultimately death.

HIV-1 treatment includes a combination of anti-HIV compounds, which target the HIV reverse transcriptase (azidothymidine (AZT), lamivudine (3TC), dideoxyinosine (ddI), tenofovir, neviparine, efavirenz), or protease (saquinavir, nelfinavir, indinavir, amprenavir, lopinavir), and only one new fusion inhibitor, enfuvirtide, has been recently approved (Richman, D. D., Nature, 2001, 410, 995-1001; Lalezari et al., N. Engl. J. Med., 2003, 348, 2175-2185). However, the emergence of new HIV isolates resistant to existing drugs, in addition to difficulties in compliance with drug regimens because of pill burden and adverse side effects, suggests that new therapies with new drugs targeting different steps of the HIV cycle are urgently needed.

Although considerable effort has been expended on the design of effective vaccine, currently no vaccine against HIV infection exists.

The HIV viral particle comprises a viral core composed of capsid proteins, RNA genome and enzymes, surrounded by a shell of myristylated gag proteins. This shell is in turn surrounded by an outer lipid membrane envelope comprising the HIV envelope glycoproteins (gp120 and gp41). The HIV envelope glycoproteins are synthesized as a single 160 kilodalton precursor protein, which is cleaved by a cellular protease during viral budding into two glycoproteins, gp41 and gp120. gp41 is a transmembrane glycoprotein and gp120 is an extracellular glyco-protein, which remains non-covalently associated with gp41. gp120 is displayed as a gp41-associated trimer and forms envelope spikes on the surface of HIV virions.

The HIV entry is a multiple-step process initiated by the binding of the HIV surface envelope glycoprotein gp120 (Env) to the host cell CD4 receptor. This association induces conformational changes in Env that allow its binding to a chemokine co-receptor CCR5 or CXCR4 (Wu et al., Nature, 1996, 384, 179-183; Trkola et al., Nature, 1996, 384, 184-187; Feng et al., Science, 1996, 272, 872-877). Association with this co-receptor activates the fusogenic properties of the non-covalently associated gp41 transmembrane protein and subsequent entry of the virus into the cell (Wyatt R. and Sodroski J., Science 1998, 280, 1884-1888).

Each of these steps can represent a potential target for new drugs (Blair et al., Drug Discov. Today, 2000, 5, 183-194; Moore J. P. and Doms R. W., P.N.A.S., 2003, 100, 10598-10602; Vermeire, K., and Schols, D., Expert. Opin. Investig. Drugs, 2005, 14, 1199-1212; Ryser H. J. P and Flückiger, R., Drug discovery today, 2005, 10, 1085-1094).

Information on the cellular receptors involved in virus infection, as well as on the viral envelope structure and its interaction with host cells, may help in the design of entry inhibitors and HIV vaccines.

The three-dimensional structure of the gp120 "core" protein has been determined in the CD4-bound conformation (gp120HXB2:CD4:17b complex; PDB code 1g9m; Kwong et al., Nature, 1998, 393, 648-659; Huang et al., Science, 2005, 310, 1025-1028; Kwong et al., Structure, 2000, 8, 1329-1339) and the more recently published unliganded form of SIV gp120 (PDB code 2BF1; Chen et al., Structure, 2005, 13, 197-211), but so far there is no crystal structure available of the gp120 trimer.

In the CD4-bound conformation, gp120 consists in an inner and an outer domain connected by a four-stranded β-sheet (bridging sheet), whereas in the unliganded conformation, although it maintains this two-domain organization, the inner domain is significantly different and the β-sheet is not formed. CD4 binding creates a cavity of roughly 150 Å$^3$, which extends deeply in the interior of gp120 at the intersection between the inner and outer domain, whereas this cavity is absent in the unliganded form.

In the complex, a large surface of the domain D1 (742 Å$^2$) of CD4 binds to a large (800 Å$^2$) conserved depression on gp120. The CD4 interface is comprised of 12 residues (positions 36 to 47 of CD4 amino acid sequence corresponding to the CDR2-like loop of CD4) contributing to gp120 binding with mixed hydrophobic, electrostatic, H-bonding interactions. In the complex, CD4 Phe43 side chain plugs the entrance of the gp120 cavity (Phe43 cavity or Phe43 pocket) and CD4 Arg59, just behind Phe43, is involved in a double H-bond with Asp368 in gp120.

Besides these cell receptors, HIV is capable of binding to other molecules present on the cells that it infects, such as DC-SIGN, sphingolipides or heparan sulphates. Heparin, sulfated polysaccharides and polyanions in general are known to bind to the V3 loop of the viral envelope gp120 (with a preference for envelopes of X4 tropism), (Harrop, H. A. and Rider, C. C., Glycobiol., 8, 131-137; Moulard et al, J. Virol., 2000, 74, 1948-1960) and to a CD4-induced (CD4i) region of gp120, close to V3, involved in co-receptor binding (Vivès et al., J. Biol. Chem., 2005, 280, 21353-21357). The association between V3 loop and those molecules seems to dominate the electrostatic effect of this double interaction and probably occurs through interactions between the acidic sulfate moieties of heparin derivatives and basic residues of V3 loop. Viruses of X4 tropism are known to have more basic V3 loops (Berger et al., Nature, 1998, 391, 240-) and would therefore be better binders to heparin derivatives. This does not exclude an affinity of heparin derivatives to the CD4i epitope of viruses of R5 tropism, since peptides containing sulfated tyrosine are also able to associate with those gp120 (Farzan et al., J. Biol. Chem., 2002, 277, 40397-40402).

Cell attachment is the first step in HIV-1 entry and a primary target for antiviral therapy and vaccine design.

Antiviral-Therapy

Different macromolecules have been demonstrated to inhibit gp120 binding to CD4, starting from soluble CD4 (Daar et al., P.N.A.S., 1990, 87, 6574-6578). However, monovalent potent inhibitors of CD4-gp120 binding such as soluble CD4 are shown to be effective in vitro (Daar et al., precited) but have reduced affinity for primary isolates. Evidence is arising that HIV-1 through its envelope trimers could bind several cell-surface CD4 receptors simultaneously (Kwong et al., Nature, 2002, 420, 678-682). Multimeric inhibitors targeting several CD4 binding sites on single spike or even on a virion could therefore be much more able to compete with CD4 for the attachment to the virus. Well-tailored multivalent ligands could lead to large avidity gains by decreasing the off-rate of the complex and increasing functional affinity of the ligand (Gestwicki et al., J. Am. Chem. Soc., 2002, 124, 14922-14933; Sadler et al., Rev. Mol., Biotech., 2002, 90, 195-229).

Only few multimeric compounds displaying several molecules of CD4 have been developed so far. Among them, complex constructs presenting four or twelve copies of CD4 domains in an immunoglobulin structure were reported (Allaway et al., AIDS Res. Hum. Retroviruses, 1995, 11, 533-539; Gauduin et al., J. Virol., 1996, 70, 2586-2592; Arthos et al., J. Biol. Chem., 2002, 277, 11456-11464) and led to promising results as HIV-1 inhibitors (Arthos et al., precited; Trkola et al., J. Virol., 1995, 69, 6609-6617). The increased stability of these molecules and the possibility that they may simultaneously block several gp120 subunits of the trimeric envelope at the surface of virions or spikes of infected cells may explain their superior antiviral potency. Nevertheless, the large size of these molecules and the possibility that they may induce an anti-CD4 auto-immune response might represent a limitation for their therapeutic applications.

However, in spite of many years of efforts worldwide, only a handful of small molecules targeting CD4 binding site on gp120 and inhibiting CD4 attachment has been discovered. The large size and complexity of the CD4 interface make the reproduction of such functional epitope into a small molecule a challenge, and explain the difficulty in the development of small molecule inhibitors of gp120-CD4 interaction.

For some time, the recently-described small molecule BMS-378806 developed by Bristol-Myers Squibb (Wang et al., J. Med. Chem., 2003, 46, 4236-4239) was believed to inhibit CD4-gp120 binding but more recent studies have demonstrated that BMS would interact with another region of gp120, thus hindering the conformational changes induced by CD4 binding (Si et al., P.N.A.S., 2004, 101, 5036-5041; Madani et al., J. Virol., 2004, 78, 3742-3752). This molecule was dimerized with a low increase in activity (Wang et al., Org. Biomol. Chem., 2005, 3, 1781-1786).

The International PCT Application WO 2005/121175 describes small molecule CD4 mimetics comprising fused bicyclic or tricyclic core structure. However, no antiviral activity has been demonstrated for these molecules.

Until now, the CD4 mimics designed from scorpion toxin scyllatoxin have remained the smallest potent inhibitors of that kind available (Vita et al., P.N.A.S., 1999, 96, 13091-13096; Martin et al., Nature Biotech., 2003, 21, 71-76; Stricher et al., Biochem. J., 2005, 390, 29-39; International PCT Application WO 02/059146). The mini-proteins mimic of CD4 were designed to reproduce the structure of the gp120 glycoprotein binding "hot spot" of the CD4 surface, on to the scaffold consisting of the scorpion (*Leiurus quinquestriatus hebraeus*) toxin scyllatoxin. This small (31-residues) toxin was selected since its structure, formed by an antiparallel β-sheet linked to a short helix by three disulphide bridges, contains an exposed positions 18-29 β-hairpin, which could superimpose its backbone atoms on those of positions 36-47 CDR2-like loop of CD4 with an r.m.s (root mean square) deviation of only 1.10 Å. On the basis of this structural similarity, the scaffold permissiveness in sequence mutations and stability, even after sequence replacements, critical functional residues of the CDR2-like loop of CD4 could be grafted on to the β-hairpin of scyllatoxin, leading to the initial low-affinity mimic (CD4M3).

A first optimization of the interactions with gp120 was achieved by structure-activity studies, leading to the first generation of mini-proteins, CD4M9. CD4M9 is able to inhibit the binding of soluble CD4 to gp120 with an $IC_{50}$ (concentration causing 50% inhibition of sCD4 binding to gp120) about a hundred-fold higher than that of native CD4. Recently Li et al. have reported a dimeric version of the first generation of CD4 mimic M9 with a twenty-fold enhanced anti-HIV activity over the monovalent molecule (Li et al., Bioconj. Chem., 2004, 15, 783-789 and US Patent Application 2005/0176642).

Further optimization was achieved with the help of the NMR structure of the CD4M9 mini-protein combined to molecular modeling, leading to the second generation of mini-proteins, CD4M33 (27 amino acids, SEQ ID NO: 1). CD4M33 is able to bind different gp120s in competition with soluble CD4 with a nanomolar $K_d$, to induce CD4-like conformational changes in gp120, exposing the cryptic epitopes necessary to target co-receptor elements, as well as to inhibit infection of primary cells by primary clinical HIV-1 isolates.

In addition, heparin or heparin fragments of sufficient size, in the presence of CD4 mini-protein interact with the CD4i domain of the gp120 and this combination greatly inhibits the gp120/co-receptors interaction, as demonstrated by inhibition of the gp120/48D or 17b antibody interaction (International PCT Application WO 03/089000).

However, HIV-1 inhibition in cell-cell fusion and virus-cell fusion assays remains less efficient with these mimics than that with CD4s.

Some of those small and stable mini-proteins were co-crystallized in complex with gp120 and antibody 17b Fab fragment (Huang et al., Structure 2005, 13, 755-768), providing precise structural information about the binding of those compounds with the gp120 binding site. The three-dimensional structure of CD4M33, free or in complex with gp120 (PDB code 1YYL) has been solved (Stricher et al., Biochem. J., 2005, 390, 29-39; Huang et al., precited). In CD4M33, Biphenylalanine 23 was shown to play a key role in the interaction with gp120 binding pocket. Another important structural feature of this mini-protein is the β-hairpin which represents the "hotspot" of the binding region to gp120 (FIG. 1), accounting with about 80% of the interface. However, the residues defining this β-turn have not been well explored in the previous studies.

HIV-Vaccine gp120 appears to be the primary target for inducing a humoral immune response to HIV. However, it has been difficult to generate protective responses against the HIV Env because the CD4 binding site is buried between the outer domain, the inner domain, and the V1/V2 domains of gp120. Thus, although deletion of the V1/V2 domain may render the virus more susceptible to neutralization by monoclonal antibody directed to the CD4 site, the conformation of Env prior to CD4 binding may prevent an antibody response.

It has been shown that CD4 and CD4 mimetics that bind to gp120 cause a conformational change in Env that exposes one or more cryptic or inducible epitopes in or near the CD4 binding site, which in turn allows the generation of a neutralizing antibody response to Env.

Therefore, the use of complexes of Env and CD4 or Env and CD4 mimics (mini-proteins derived from scyllatoxin or small cyclic molecules) as vaccine to generate a protective immune response against HIV has been proposed (International PCT Applications WO 2004/037847 and WO 2005/121175).

The use of small CD4 mimics should prevent the risk of inducing an anti-CD4 auto-immune response that might occur when using the CD4 molecule. Unlike CD4, CD4M33 was shown to be low immunogenic as indicated by lower level and antibodies induced by the mini-protein. Moreover, anti-CD4M33 antibodies did not cross-react with CD4. Therefore, the use of CD4M33 in a vaccine may be safer compared to CD4.

SUMMARY OF THE INVENTION

To improve CD4M33 affinity, crucial for in vivo HIV-1 neutralization efficiency, the inventors have explored the synergetic contribution of (L)- and (D)-amino acids at four positions of the mini-protein, by combinatorial chemistry. After iterative deconvolution of the generated libraries, two peptides, named CD4M47 and CD4M48, possess sub-nanomolar affinities for a wide range of gp120 isolates and an up-to-tenfold enhanced neutralization potency compared to CD4M33. Both peptides stabilize the CD4-bound conformation of gp120, which was confirmed by 3D co-crystallographic complex with core gp120YU2 and 17b Fab and by direct binding to CCR5$^+$ cell lines.

A straightforward synthesis of multimers of the mini-CD4 and its covalent linkage to an inhibitor targeting other critical interactions led to compounds that exhibit remarkable anti-viral properties.

The CD4 mimic CD4M48 was dimerized and tetramerized to target several CD4 binding sites on a spike, using polylysine constructs with arms to various lengths. In these constructs, the mini-protein keeps its ability to bind with high affinity to the CD4 binding site and shows slower dissociation constants by displaying a higher local concentration of binding elements. This remarkable enhancement of avidity termed also "functional affinity" resulted in a greatly enhanced neutralization activity. Dimers, for example, show a 2-log increased potency compared to the monomer in cell-cell fusion and infection assays for most of tested isolates. It is notable that compared to CD4M9 dimerization, CD4M48 dimerization induces a much greater enhancement in neutralization activity.

To prevent the other critical interactions with the cell, mainly the binding to the co-receptor, a hetero-bivalent inhibitor was also synthesized. Hetero-dimer CD4M48–heparin designed to target simultaneously CD4 binding site and the V3 loop of gp120 also demonstrates interesting biological properties. As for homo-dimers, the high affinity of the mini-CD4 is conserved in this latter complex. Moreover, its covalent linkage with heparin allows the inhibition of the recognition of the CD4i epitopes by neutralizing antibodies for a series of envelopes, independently from co-receptor usage. Besides CD4M48–heparin blocks the infection in primary cells by some HIV-1 isolates much more efficiently than CD4M48. Biological data obtained for that molecule outlined the possible increased efficiency that could be achieved by combining different inhibitors of gp120 binding to multiple targets.

These new homo- or hetero-bivalent molecules could therefore be of first interest for therapeutic applications in the development of HIV-1 entry inhibitors and underline the relevance of designing multiple target inhibitors for the development of highly potent new anti-HIV-1 agents. In addition, their good solubility in water will be a great asset for the formulation of gels or creams to be used as topical microbicides, as an alternative to other preservatives to prevent sexual transmission.

The binding of the peptide of the present invention to Env polypeptides induces a conformational change in Env which unmasks cryptic neutralizing epitopes in or near the CD4 binding site. Therefore, the peptides of the present invention can also find vaccine applications. They also make it possible to design novel molecules, which are of use, for example in the detection, and also in the purification of the envelope protein of HIV and in the discovery of new anti-HIV drugs.

The invention relates to an isolated peptide, characterized in that it comprises the following sequence (I):
TPA-Asn-Leu-His-Phe-Cys-Gln-Leu-Xaa$^a$-Cys-Lys-Ser-Leu-Gly-Leu-Leu-Gly-Arg-Cys-Xaa$^b$-Xaa$^c$-Xaa$^d$-Xaa$^e$-Cys-Ala-Cys-Val-NH$_2$ (SEQ ID NO: 2) wherein TPA represents thiopropionic acid, Xaa$^a$ represents Arg or Lys, Xaa$^b$ represents Ala or Arg, Xaa$^c$ represents a D-amino acid, Xaa$^d$ represents Thr, Ser or Asn, Xaa$^e$ represents phenylalanine or a phenylalanine derivative having the structure (II):

$$H_2N\diagdown\diagup COOH$$
$$\text{—A—(B)}n\text{—R,}$$

where A is absent or represents S, O, NH or CH$_2$, B is absent or represents a C$_1$ to C$_6$ branched or straight-chain alkyl, and R represents a C$_3$ to C$_6$ alkyl, heteroalkyl, cycloalkyl, heterocycloalkyl, cycloalkenyl, cycloheterocyloalkenyl, aryl, or heteroaryl.

DEFINITIONS

"D-amino acid" refers to the D optical isomer of any natural amino acid except glycine which is achiral and their analogs, both naturally occurring and synthesized.

"CD4 mimetic" refers to a molecule that binds to the CD4 binding-site of the gp120. The terms "CD4 mimetic", "CD4 mimic", "CD4 mimic mini-protein", "CD4 mini-protein", "mini-protein", "CD4 mimic peptide", "CD4 peptide", "peptide", are used interchangeably.

"CD4i epitope" refers to an epitope of gp120 which is induced by the binding of CD4.

The peptide of the present invention comprises two mutations compared to CD4M33. The mutation Lys 18Arg, and the mutation of Gly21 to a D-amino acid. In addition, amino acid variation is introduced in positions 9, 20, 22 and 23. The arginine residue in position 9 may be replaced by a lysine. The alanine residue in position 20 may be replaced by an arginine. The serine residue in position 22 may be replaced by another small and polar amino acid such as a threonine or an asparagine. The residue in position 23 may be a phenylalanine or a phenylalanine derivative of the structure (II) as defined above.

Compared to CD4M33, the β-hairpin structure of the peptide according to the invention comprises a stabilized type II' β-turn. Moreover, fine structural interfaces analyses show that the optimized residues of the peptide according to the invention increase the contact surface of about 40 Å$^2$, which represents about 10% of the total mimetic contact surface. Like CD4M33, the peptide binds to gp120 with sub-nanomolar affinities for a wide range of gp120 isolates. Stabilizing of the type II' β-turn and increasing the contact surface area in the peptide according to the present invention lead to a significant increase (up-to-ten-fold) of its neutralization potency of HIV infection, compared to its parent molecule [Phe$^{23}$] CD4M33. 3D co-crystallographic complex with core gp120YU2 and 17b Fab and direct binding to CCR5$^+$ cell lines, confirm that the peptide of the invention is able to induce a stabilization of the CD4-bound conformation of gp120, which is equivalent to that induced by CD4.

In a preferred embodiment, the invention features a peptide wherein Xaa$^a$ is lysine (Lys).

In another preferred embodiment, the invention features a peptide wherein Xaa$^b$ is alanine (Ala).

In another preferred embodiment, the invention features a peptide wherein Xaa$^c$ is (D)proline ((D)Pro).

In another preferred embodiment, the invention features a peptide wherein Xaa$^d$ is threonine (Thr).

In another preferred embodiment, the invention features a peptide comprising a phenylalanine derivative of the structure (II) wherein B represents a $C_1$ to $C_3$ straight-chain alkyl. Preferably, the phenylalanine derivative of the structure (II) is selected from the group consisting of: para-cyclo-hexyl-methoxyphenylalanine and para-cyclo-pentylethoxyphenylalanine.

In another preferred embodiment, the invention features a peptide comprising a phenylalanine derivative of the structure (II) that is a biphenylalanine.

Preferred peptides according to the present invention are the peptides having any of the sequences SEQ ID NO: 3 (CD4M47), SEQ ID NO: 4 (CD4M48), SEQ ID NO: 5 (CD4M48_U1) and SEQ ID NO: 6 (CD4M48_U2). A more preferred peptide is the peptide of the sequence SEQ ID NO: 5 (CD4M48_U1).

In another preferred embodiment, the invention features a peptide having a Lys residue in position 9 or 11 that is modified by a thiol, an hydrazino group, a maleimido group, or a N-hydroxysuccinimidylester. These residues do not interfere with the binding to the gp120. For example, in the trimeric model of gp120 in interaction with three peptides according to the present invention (FIG. 14), Lys11 is at the opposite face of the binding region and as result does not interfere with the binding. The synthesis and the folding of the peptide with a supplementary thiol do not bring any difficulty provided that refolding is performed in reduced conditions, for example in the presence of 5 mM of reduced glutathione. Therefore, these residues can be used to incorporate chemical functions which can be used to chemoselectively ligate compounds of interest. The compound of interest may be a peptide according to the present invention, so as to form multimers. The compound may also be a probe to form a labelled peptide for detecting the Env protein or for screening other inhibitors of CD4 binding to gp120. Furthermore, the compound may be another inhibitor of HIV-1 entry to form a multivalent antiviral agent.

The peptide according to the present invention may be in the form of a monomer or an oligomer, preferably said peptide is a dimer.

According to the present invention, the oligomer comprises at least two peptides linked to one another by a spacer of a length which is appropriate for binding of the peptides to the CD4 binding sites on the trimeric HIV gp120 complex. Preferably, the length of the spacer spans the distance between two CD4 binding sites on the trimeric HIV gp120 complex, most preferably, the length of the spacer is from 30 Å to about 100 Å. The spacer is advantageously bivalent or trivalent. Furthermore, the spacer is linked preferably to a peptide residue which does not interfere with the binding to the gp120, more preferably to the Lys residue in position 11 or a chemically modified derivative from said Lys residue, as defined above.

The spacer may be any polymer of appropriate length, preferably soluble in aqueous buffers. This spacer may be designed and based on a large variety of linkages, such as, for example, polyglycols, polyamines, a mix of polyamides and amines (PAMAM), poly(arylether). It may be, for example, polyethylene glycol: $(CH_2CH_2O)_n$.

In addition, the peptide according to the present invention may be advantageously labelled with an appropriate probe (radioactive isotope, fluorescer, chemoluminescer, enzyme, chromophore, dye, metal ion, ligand) to allow the detection of the HIV Env protein or to use as tracer for the screening of other molecules which bind to the CD4 binding site of the gp120.

The invention relates also to a multivalent antiviral compound, characterized in that it comprises at least one peptide as defined above, linked to an HIV entry inhibitor selected from the group consisting of: co-receptor-gp120 binding inhibitors and viral-cell fusion inhibitors.

The inhibitor is linked preferably to a peptide residue which does not interfere with the binding to the gp120, more preferably to the Lys residue in position 9 or 11, or a chemically modified derivative of said Lys residues, as defined above.

In addition the peptide and the inhibitor may be linked via a spacer arm. The spacer arm may be any polymer of appropriate length, in order to allow the hybrid formed to bind to all its targets on the gp120 viral protein. Preferably, the polymer is soluble in aqueous buffers. This spacer may be designed and based on a large variety of linkages, such as, for example, polyosides, polyglycols, polyamines, a mix of polyamides and amines (PAMAM), poly(arylether). It may be, for example, polyethylene glycol: $(CH_2CH_2O)_n$.

In a preferred embodiment of the multivalent antiviral compound according to the invention, the peptide is linked to a polyanion, for example heparin or heparin sulphate. This compound inhibits both gp120/CD4 and gp120/coreceptors interaction. The various polyanions described in the PCT Application WO 03/089000 can be used in the present invention.

According to another preferred embodiment of the multivalent anti-viral compound according to the present invention, the peptide is linked to an HIV inhibitor which binds to the gp120 co-receptor; CCR5, CCR3, CXCR4 inhibitors/antagonists are one example of such inhibitors.

The invention relates also to an antiviral composition comprising at least one peptide and/or or one multivalent compound as defined above, in an acceptable carrier, such as stabilizer, buffer and the like.

A pharmaceutical composition or formulation refers to a form suitable for administration, e.g., systemic or local (topical) administration, into a cell or subject, including for example a human. Suitable forms, in part, depend upon the use or the route of entry, for example oral, topical, inhalation, or by injection. A preferred formulation is an antiviral gel or a cream for topical administration.

In another embodiment, the antiviral composition according to the present invention, further comprises at least one additional anti-HIV drug.

The invention relates also to the use of a peptide or a multivalent antiviral compound as defined above for the manufacture of a medicament intended for the prevention or the treatment of HIV infection in a subject.

The invention relates also to a product containing a peptide or a multivalent antiviral compound as defined above, and an anti-HIV drug, as a combined preparation for simultaneous, separate or sequential use in anti-HIV therapy.

The anti-HIV drugs which are used in combination with the peptide/multivalent compound according to the invention are those commonly used in anti-HIV therapy, and include molecules targeting the HIV reverse transcriptase (nucleosidic:Azidothymidine (AZT), Zidovudine (ZDV), Lamivudine (3TC), Dideoxyinosine (ddI), Tenofovir (TDF), Abacavir (ABC), Stavudine (d4T), and non-nucleosidic:Neviparine (NVP), Efavirenz (EFZ), Delavirdine (DLV)), the protease (Saquinavir (SQV), Nelfinavir (NFV), Indinavir (IDV), Amprenavir, Lopinavir, Ritonavir (RTV)), as well as inhibitors of HIV entry such as co-receptor-gp120 binding inhibitors, for example CCR5, CCR3 or CXCR4 inhibitors/antagonists, and fusion inhibitors (T20). The anti-HIV drugs are used in combination, as for example: d4T, 3TC and NVP; ZDV, 3TC, and NVP; d4T, 3TC, and EFZ; ZDV, 3TC, and EFZ. A combination which targets different stages in the infectious process and is likely to be more efficacious is preferred. For instance, it is known that fusion inhibitor (T20) and CXCR4 antagonist (AMD3100) have synergistic effect.

The invention relates also to an immunogenic composition, characterized in that it comprises at least a complex of a peptide as defined above, and an HIV Env polypeptide, in an acceptable carrier, such as stabilizer, buffer and the like.

The peptide of the present invention binds to the CD4 binding site on the gp120 protein and is able to induce a conformational change in the Env poly-peptide which exposes epitopes that elicit neutralizing antibodies.

The HIV Env polypeptide may be the gp120 or an immunogenic fragment thereof.

The gp120 may be in the form of a monomer or an oligomer. Preferably the gp120 is a trimer.

The immunogenic fragments of gp120 are well-known to those of ordinary skill in the art. Preferred fragments include gp120 variants wherein the entire V1V2 region or the V2 loop are deleted, or the V3 loop is site-specifically deglycosylated; these modifications in gp120 expose neutralization epitopes and render the mutant viruses more susceptible to antibody-mediated neutralization.

The vaccine composition may further comprise an adjuvant, another HIV antigen or an immunoregulatory agent. Suitable adjuvants, HIV antigens and immunoregulatory agents are well known to those of ordinary skill in the art.

The invention relates also to the use of a complex as defined above for the manufacture of a vaccine, intended for the prevention or the treatment of HIV infection in a subject.

The invention relates also to a product containing a complex as defined above, and an HIV antigen or immunoregulatory agent, as a combined preparation for simultaneous, separate or sequential use in anti-HIV vaccination (prophylactic or therapeutic).

A pharmaceutically effective dose is that dose required to prevent, inhibit the occurrence or treat (alleviate a symptom to some extent, preferably all the symptoms) of a disease or state. The pharmaceutically effective dose of the peptide/multivalent compound/complex depends upon the composition used, the route of administration, the type of mammal being treated, the physical characteristics of the specific mammal under consideration, concurrent medication, and other factors, that those skilled in the medical arts will recognize. Generally, an amount between 0.01 mg/kg to 1000 mg/kg, preferably 10 mg to 500 mg body weight/day of active ingredients is administered.

The peptide/complex/multivalent compound of the invention may be administered by a single or multiple route(s) chosen from: topical (transcutaneous, rectal, vaginal, nasal), parenteral (percutaneous, subcutaneous, intravenous, intramuscular, intraperitoneal and intrarachidian), oral, sub-lingual, inhalation or intracerebral (intrathecal, intraventricular).

The invention relates also to the use of the peptide as defined above for the manufacture of a diagnostic reagent, intended for the detection of HIV infection in a subject. The presence of HIV virions in a biological sample is assessed by detecting the formation of gp120/peptide complexes. Means for detecting such complexes are well-known in the art.

The invention relates also to a method of producing HIV neutralizing antibodies, comprising the steps of:
   administering a complex as defined above to a subject under conditions that allow the production of antibodies (monoclonal or polyclonal neutralizing antibodies); and recovering antibodies from said subject, by any means.

The invention relates also to the use of the peptide as defined above, for the detection or for the purification of the HIV Env protein. The Env protein form complexes with the peptide according to the present invention and the resulting complexes are purified or detected by any appropriate method which is well-known in the art.

The invention relates also to the use of the peptide as defined above, as tracer (competitor) for screening molecules which inhibit the interaction of gp120 or of its analogues, with the CD4 molecule or its mimics, to select new molecules of interest for the manufacture of new anti-HIV medicines.

The practice of the present invention will employ, unless otherwise indicated, conventional methods of chemistry and viral immunobiology within the skill of the art. Such techniques are explained fully in the literature.

The peptides of the present invention are prepared by conventional techniques of solid-phase chemical synthesis. The chemical synthesis can be carried out, for example, by Fmoc chemistry which uses the fluorenylmethyloxycarbonyl group for temporary protection of the alpha-amino function of the amino acids.

Preparation of spacer arms which can be used in the present invention have been widely described in the prior art (Greenwald et al., Advanced Drug Delivery Reviews, 2003, 55, 217-250; Vernese et al., Il Farmaco, 1999, 54, 497-516).

For example, multivalent peptides may be based on polylysine constructs. They are synthesized on solid support and reacted with PEGylated linkers to span the distance between two CD4 binding sites and a maleimido group is finally introduced on each arm so that they can be chemoselectively ligated in solution to a thiol derivative of the peptide according to the present invention (FIG. 15).

The linking of the peptide to a polyanion is formed by any techniques known to those skilled in the art. For example, the various methods described in Chernyak et al., Carbohydr. Res., 2001, 330, 479-486; Kuberan et al., Glycoconj. J., 1999, 16, 271-281; Najjam et al., Cytokine, 1997, 9, 1013-1022, can be used in the present invention. Preparation of spacer arms is described for example in Dreef-Tromp et al., Biorg. Med. Chem. Lett., 1998, 8-16, 2081-2086 and Grootenhuis et al., Nat. Struct. biol., 1995, 2, 736-739.

The various Env polypeptides and the methods for preparing Env-CD4 mini-protein complexes which are described in the International PCT Application WO 2004/037847CD4 can be used in the present invention.

The compositions or formulations are prepared according to any method known in the art for the manufacture of pharmaceutical compositions.

The antibodies are produced by conventional methods.

The screening is achieved by any competition binding assay, for example by using the fluorescence anisotropy technique described in the PCT Application WO 03/005032 and in Stricher et al., Biochem. J., 2005, 390, 29-39.

BRIEF DESCRIPTION OF THE DRAWINGS

In addition to the preceding features, the invention further comprises other features which will emerge from the description which follows, which refers to examples illustrating the CD4 mimic mini-protein and their uses according to the invention, as well as to the appended drawings in which:

FIG. 2 illustrates the iterative deconvolution strategy for the search of biologically optimal residues at positions 18, 20, 21 and 22 of CD4M33.

FIG. 3 represents the CD spectra of the four libraries used in the study.

FIG. 11 illustrates the synthesis of phenylalanine derivatives with para[c-alkyl or c-aryl alcoxy chain], using the synthetic route described by A. D. Morley (Tetrahedron Lett., 2000, 41, 7405-7408).

FIG. 15 represents a series of dimers and tetramers of CD4M48 based on polylysine constructs. CD4M48 was ligated via a supplementary mercapto group to polylysine constructs including PEGylated linkers and maleimido groups, where PEGi stands for a linker of desired length (30, 50 or 100 Å), M48D stands for CD4M48 dimer and M48T stands for CD4M48 trimer.

EXAMPLE 1

Figure 1:
FIG. 1 represents a close-up view of the α/β tertiary ribbon representation (Koradi et al., J. Mol. Graph., 1996, 14, 51-55, 29-32) of CD4M33 mini-protein in contact with the binding pocket surface of gp120 (PDB code 1YYL; Huang et al., Structure, 2005, 13, 755-768). Amino acid side chains are in grey, and disulfide bonds, crucial of the scyllatoxin-scaffold are in white. Mutations introduced in the sublibraries are highlighted in black.

Engineering of a CD4 Mimic Mini-Proteins by Combinatorial Chemistry

1) Experimental Procedures
a) Material

All N-Fmoc (fluoren-9-ylmethoxycarbonyl)-protected amino-acids, N,N'-dicyclohexylcarbodiimide (DCC) and O—(N-Fmoc-2-aminoethyl)-O'-(2-carboxyethyl)undeca-ethyleneglycol were purchased from NOVABIOCHEM. Fmoc PAL-PEG-PS resin (0.2 mmol/g) was purchased from APPLIED BIOSYSTEMS. Fmoc-Bip-OH was from BACHEM or ADVANCED CHEMTECH. Fmoc-8-amino-3,6-dioxaoctanoic acid was from NeoMPS. All other reagents and solvents used were from SIGMA-ALDRICH and FLUKA or SDS (SOLVANTS DOCUMENTATION SYNTHESES). Alexa-488 succinimidyl ester was from MOLECULAR PROBES. X4-tropic LAI recombinant gp120 produced in mammalian cells (CHO) was provided by PROGENICS. R5-tropic SF162 and Dual-tropic SF2 recombinant gp120s were produced in mammalian cells (CHO). X4-tropic HXB2 and R5-tropic YU2 recombinant gp120s were produced in baculovirus expression system, as described in Misse et al., J. Virol., 72, 7280-7288 and Mechulam et al., J. Mol. Med., 2005, 83, 542-52. 4-domain recombinant sCD4 was obtained from PROGENICS. CHO-CCR5+ cells are described in Samson et al., Biochemistry, 1996, 35, 3362-3367 and Blanpain et al., Blood, 2000, 96, 1638-1645.

b) Peptide Synthesis.

All combinatorial libraries and individual peptides were synthesized on an Advanced Chemtech 357 Multisynthesizer by solid phase method using fluorenylmethyloxycarbonyl (Fmoc)-protected amino-acids and 2-(1-H-Benzotriazol-1-yl)-1,1,3,3-tetramethyluronium hexafluorophosphate (HBTU) coupling reagent (Carpino L. A., J. Am. Chem. Soc., 1993, 115, 4397-4398).

$b_1$) Combinatorial Libraries Synthesis

Each sub-library was synthesized using 33 µmol Fmoc-PAL-PEG-PS-resin (PERSEPTIVE BIOSYSTEMS). The 10 first residues were introduced by 10 molar equivalent Fmoc-protected amino-acids, using 9.1 equivalent HBTU and 22 equivalent N,N-Diisopropylethylamine (DIEA), during 30 minutes. The end of the synthesis was performed using double coupling steps with half the previous quantities. The last residue was incorporated as a 3,3'dithiopropionic acid moiety. To introduce variability at the desired positions, the resin was collected prior to coupling, mixed in N-methylpyrrolidone/Dichloromethane (50/50) by nitrogen flow and equally divided into n wells (where n is the number of different amino acids we wanted to couple). This process, called "split and mix" method, was repeated for each variable position so that, if we consider a peptide with a variability of n, n' and n" amino acids at three different position, we end up with n wells containing n'×n" peptides each. The resin was finally treated with tributylphosphine for 1.5 h, washed and the sub-libraries cleaved by treatment with reagent K' (81.5% trifluoroacetic acid, 5% water, 5% phenol, 5% thioanisole, 2.5% ethanedithiol, 1% triisopropylsilane) for 2.5 h at room temperature. After one hour precipitation in diethyl oxide, the peptides were washed and lyophilized. Disulfide bridges were formed with the sub-libraries dissolved at 0.4 mg/mL in 100 mM TrisHCl buffer (pH 7.8) in the presence of 0.5 mM/5 mM oxidized/reduced glutathione. The sub-libraries were purified by reverse-phase HPLC on a C18 Discovery column (10×250 mm) (SUPELCO) and their composition was verified by quantitative amino acid analysis and MALDI-TOF mass spectrometry. Finally, the peptide libraries were analyzed by circular dichroism (CD) on a Jobin Yvon CD6 dichrograph. Optimization of the combinatorial protocols and synthesis of individual peptides were performed on an ABI-433 automated peptide synthesizer (APPLIED BIOSYSTEM). The fluorescent peptides were labelled by the specific incorporation of Alexa-488 at $Lys^{11}$, protected during synthesis with 1-(4,4 dimethyl-2,6-dioxocyclohex-1-ylidene-3-methylbutyl) (ivDde) (Chhabra et al., Tetrahedron Lett., 1998, 39, 1603-1606). Amino acid compositions were made under standard conditions: samples were vacuum-dried, sealed in glass tubes and hydrolyzed under vapor phase of 6N HCl with a crystal of phenol through 17 h at 110° C. Amino acids were derivatized with ninhydrin and quantified on an aminoTac JLC-5001V amino acids analyzer (JEOL). Circular dichroism analyses were made on a Jobin Yvon CD6 dichrograph, in a quartz cuvette of 1 mm. Spectra in far UV (180-250 nm with 0.5 nm steps) were obtained using 200 µL of each sample at $5 \cdot 10^{-5}$ M in 2 mM phosphate buffer, pH 7.4, by accumulating 4 spectra with 0.5 seconds integration every step.

$b_2$) Individual Peptides Synthesis

CD4M48 was synthesized on an ABI-433A (APPLIED BIOSYSTEMS) automated peptide synthesizer, using the stepwise solid-phase method and standard Fmoc chemistry. Synthesis was performed on a 0.1 mmol scale with 10 eq. Fmoc-protected amino-acids, 20% piperidine in NMP for Fmoc-deprotection, DCC and Cl-HOBt for activation, and acetic anhydride for capping. N-terminal thiopropionyl group (Tpa) was introduced as its disulphide. The mini-protein was cleaved from the resin with simultaneous removal of side-chain protecting groups by treatment with reagent K' [TFA/H₂O/Phenol/Thioanisole/EDT/TIS: 81.5/5/5/5/2.5/1 (all v/v)] for 2.5 h at room temperature. The resin was then filtered off and the fully deprotected peptide was precipitated in methyl t-butyl ether at 4° C. After centrifugation and washing with methyl-t-butyl ether, CD4M48 was dissolved in 20% (v/v) acetic acid and freeze-dried. To form disulphide bonds, the crude reduced peptide was dissolved (0.1 mg/mL) in 0.1 M Tris/HCl buffer, pH 8.0, containing 5.0 mM GSH and 0.5 mM GSSG. After 30 min, oxidation was stopped by acidification to pH 3.0 with HCl. The oxidized peptide was then purified by RP-HPLC, (Supelco 567212-U C18 preparative column, 10 mL/min flow rate, 0-50% acetonitrile in aq. 0.1% trifluoroacetic acid over 90 min). The identity of the purified products was verified by amino acid analysis and ESI-MS.

c) Binding Assays.

$c_1$) ELISA

Competition binding assays in ELISA were performed in 96-wells plates (MAXISORB). Briefly, 50 ng per well of antibody D7324 (AALTO BIO REAGENTS) were coated overnight at 4° C. Wells were then saturated with PBS 3% BSA buffer, washed 3 times, and 5 ng per well of gp120HXB2 or specified isolates were added, followed by addition of 250 pg of sCD4 (PROGENICS) and different concentrations of soluble competitors. After one night at 4° C., anti-CD4 mAb L120 (Centralised Facility for AIDS Reagents, NIBSC), goat anti-mouse peroxidase-conjugated antibody (JACKSON IMMUNORESEARCH), and the 3,3',5,5'-tetramethylbenzidine substrate, were added successively (SIGMA). After acidification, optical density was measured at 450 nm and expressed as the mean of duplicate (Moore, J. P., AIDS, 1990, 4, 297-305).

$c_2$) Fluorescence Anisotrophy

Binding assays by fluorescence anisotropy were made in a LJL Analyst (LJL BIOSYSTEMS) microplate reader using 384-wells plates. All peptides were diluted in 10 mM sodium phosphate buffer, pH 7.0, with 135 mM NaCl and 0.05% Tween 20.

Competitive binding assays for screening were performed as previously described (Stricher et al., Biochem. J., 2005, 390, 29-39), in a final volume of 21 μL by using 1 nM fluorescein-CD4M33, 12.5 nM gp120$_{HxB2}$ or 6 nM gp120SF162 and serial dilutions of the mini-proteins ($10^{-6}$, $10^{-7}$ and $10^{-8}$ M of each peptide sub-library). Fluorescence anisotropy was determined after 40 min equilibration time at room temperature, using 485 nm excitation and 530 nm emission filters and an additional 505 nm dichroic filter. All experiments were performed in duplicate.

Direct binding assays of fluorescent peptides were performed in triplicates by adding 10 μL of 0.5 nM Alexa-labeled mini-proteins and 10 μL of serial dilutions (two-thirds dilutions in 16 wells, starting at 200 nM) of gp120 SF2, SF162, BaL, IIIB and YU2. Collected data were fitted to the following equation using a non-linear regression program (Prism, GraphPad software Inc.):

$$A = A_f + (A_b - A_f)\frac{(L_t + R_t + K_d) - \sqrt{(L_t + R_t + K_d)^2 - 4R_tL_t}}{2L_t} \quad (1)$$

where A, $A_f$ and $A_b$ are respectively the measured, free and fully bounded anisotropy, $L_t$ is the total labeled mini-protein concentration, $R_t$ is the total gp120 concentration and $K_d$ the thermodynamic dissociation constant.

d) FACS Analysis of CD4M48-Induced Envelope Conformational Change

Adherent CHO-K1 cells expressing CCR5 (Samson et al., Biochemistry, 1996, 35, 3362-3367; Blanpain et al., Blood, 2000, 96, 1638-1645) were used to analyze gp120SF162 conformational change in complex with different mini-proteins, by FACS (BECKTON DICKINSON). Briefly, 0.03 μg of gp120SF162 were pre-incubated overnight at 4° C. in absence or in presence of 10 nM CD4 or 10 nM mini-proteins and further added to 2×10$^5$ cells in HAM F12 supplemented with 10% SVF, 1% penicillin/streptomycin. After 1 h incubation at room temperature, cells were washed 3 times with phosphate buffer saline (PBS) containing 5% BSA. Bound gp120 was subsequently stained with D7324 antibody (AALTO BIO REAGENTS) washed and labeled with goat anti-sheep secondary antibody conjugated to phycoerythrin (PE) (R&D SYSTEMS). After final wash, cells were analyzed for envelope binding by FACS.

e) Crystallization and Structure Determination

Crystals of CD4M47 (or CD4M48) were grown as a ternary complex between YU2 core gp120 and the antigen-binding fragment (Fab) of the 17b antibody. Protein production, crystal growth and data collection were carried out using procedures described previously for CD4M33 (Huang et al., Structure, 2005, 13, 755-768). Briefly, YU2 core gp120 produced in Drosophila cells, and deglycosylated with Endo H and Endo D. The deglycosylated protein was combined with CD4M47 (or CD4M48) and purified by Superdex S200 gel filtration chromatography. The complex peak was combined with Fab 17b, concentrated, and again subjected to Superdex S200 chromatography, to obtain pure ternary complex. As previously described for CD4M33 (Huang et al., precited), crystals were grown from mixtures of high molecular weight PEG and isopropanol, cross-linked by vapour diffusion glutaral-dehyde (Lusty et al, J. Appl. Crystallogr., 1999, 32, 106-112), briefly placed in a cryosolution of 20% ethylene glycol, 10% 2R-3R butandiol, mounted in a cryoloop and flashcooled in a nitrogen stream (100° K). X-ray diffraction data were collected (1.0 Å wavelength, beamline ID-22, Advanced Photon Source) and processed with HKL2000 (Otwinoski and Minor: *Processing of X-ray Diffraction Data Collected in Oscillation Mode*, W Academic Press, 1997). Refinement was carried out with CNS (Brunger et al, Acta Crystallogr. Biol. Crystallogr., 1998, 54, 905-921), using O (Jones et al., Acta Crystallogr. A., 1991, 47, 110-119), for interactive model building. The space group, P21, and lattice were isomorphous with the previously described CD4M33 ternary complex crystals (pdb id 1YYL) (Huang et al., precited). After rigid-body refinement using CD4M33 as the starting model, the CD4M47 and CD4M48 structures were built with reference to the mimetic sequences and inspection of difference electron density maps. Refinement used torsion-angle simulated annealing with slow cooling, iterative manual fitting, automated water placement, and positional and individual isotropic B factor refinement. Noncrystallographic symmetry restraints were used in the initial stages of refinement and later removed. An Rfree test set consisting of 10% of the data was used as a monitor throughout the refinement.

f) HIV Infection Neutralization Assays

For the acute infection assay in PM1 cell line (Lusso et al., J. virol., 1995, 69, 3712-3720), an immortalized CD4$^+$ CCR5$^+$CXCR4$^+$ T-cell clone susceptible of a wide variety of HIV-1 strains, the cells were seeded at 2.5×10$^4$ cells/well into flat-bottom 96-well plates in 200 μL of complete RPMI medium. Cells were then exposed to the viral stocks (~50 TCID$_{50}$/well) pre-treated or not with serial dilutions of inhibitors for 30 min. After overnight incubation at 37° C., the cells were washed twice and recultured in complete RPMI medium supplemented with the appropriate inhibitors. After 3, 5 or 7 days, the culture supernatant was removed from p24 antigen testing and replaced with fresh medium containing the appropriate inhibitors. The extracellular p24 concentrations were measured by capture ELISA, using a sandwich of specific antibodies (AALTO BIO REAGENTS).

The antiviral activity of the molecules in MT-4 cells was determined using a tetrazolium-based colorimetric assay (Hase et al., Biochem. Pharmacol., 2005, 70, 752-761). Briefly, five-fold dilutions of the test compounds in 100 μL of medium were added to duplicate wells of 96-well flat bottom plates (IWAKI). Then 6×10$^4$ MT-4 cells were added in 50 μL of medium, and finally 50 μL of diluted HIV-1 stocks was added to each well. Cytopathic effect induced by the virus was monitored by daily microscopic evaluation of the virus-infected cell cultures. At day 4-5 after infection, the cell viability was assessed via the in situ reduction of the tetrazolium compound MTS, using the CellTiter 96® AQ$_{ueous}$ one solution cell proliferation assay (PROMEGA). The absorbance was then measured at 490 nm with a 96-well plate reader and compared with four cell control replicates (cells without virus and drugs) and four virus control wells (virus-infected cells without drugs). The IC$_{50}$ was calculated for each compound from the dose-response curve.

The acute infection assays in primary cells were performed as described by Schols and coworkers (Balzarini et al., J. Biol. Chem., 2005, 280, 41005-41014). Briefly, PBMC from healthy donors were isolated by density gradient centrifugation and stimulated by phytohemagglutinin (PHA; SIGMA) in RPMI 1640 medium supplemented with 10% foetal calf serum (FCS; BIOCHROM). PBMC were infected by exposing cells (0.5×10$^6$/well; 48-well plate) to the viral stocks added at a final dose of 250 pg of p24/mL in the presence or the absence of the inhibitors. Cell supernatant was collected at day 12, and HIV-1 core Ag in the culture supernatant was analysed by a p24 Ag enzyme-linked immunosorbent assay kit (PERKIN ELMER).

Alternatively, plasma samples were assayed for Nab activity using a modification of a HIV entry assay (Wei et al, Nature, 2003, 422, 307-312) that uses the surface adherent HeLa cell-derived JC53BL-13 cell line (NIH AIDS Research and Reference Reagent Program catalogue no. 8129, TZM-B1). JC53BL-13 cells are genetically modified and selected so as to constitutively co-express CD4, CCR5 and CXCR4. The cells contain integrated luciferase and β-gal genes under tight regulatory control of an HIV-1 LTR, and they are comparable to human peripheral blood mononuclear cells (PBMCs) in susceptibility to infection by R5 and X4 viruses (Wei et al, Antimicrob. Agents Chemother., 2002, 46, 1896-1905). Pseudotyped virus was prepared in 293T cells and titred by β-gal expression on JC53BL-13 cells. $4·10^4$ JC53BL-13 cells were plated in and cultured overnight in DMEM supplemented with 10% fetal calf serum (FCS). 1,000 infectious units of pseudotyped virus were combined in a total volume of 125 µl with five-fold dilutions of test plasma beginning at 10% vol/vol in DMEM plus 1% FCS and incubated for 1 h at 37° C. Normal human plasma (NHP) was added to maintain an overall 10% concentration. Virus was then added to JC53BL-13 cells in an equal volume (125 µl) of DMEM plus 1% FCS and 80 µg ml$^{-1}$ DEAE dextran. This brought the concentration of DEAE dextran to 40 µg ml$^{-1}$ and that of human plasma to 5%, which was used as the basis for calculating neutralization titres. After 2 h at 37° C., 400 µl of DMEM plus 10% FCS, test plasma, and NHP were added, keeping the total human plasma concentration at 5%. Cells were incubated at 37° C. for two days. The assay was also adapted to a 96-well format in which 100-µl aliquots of virus-plasma mixture in DMEM containing 5% FCS and 40 g ml$^{-1}$ DEAE dextran were added to 104 JC53BL-13 cells from which media was completely removed. Cells were analysed for L-gal or luciferase expression after two days. Controls included cells exposed to no virus and to virus without test plasma or NHP. Relative infectivity was calculated by dividing the number of luciferase units at each dilution of test plasma by values in wells containing NHP but no test plasma.

2) Results a) Choice of the Mutated Positions in CD4M33

The three-dimensional structure of CD4M33, free or in complex with gp120 (PDB code 1YYL) has been solved (Stricher et al., Biochem. J., 2005, 390, 29-39; Huang et al., precited). In CD4M33, Biphenylalanine 23 was shown to play a key role in the interaction with gp120 binding pocket. Another important structural feature of this mini-protein is the β-hairpin which represents the "hotspot" of the binding region to gp120 (FIG. 1), accounting with about 80% of the interface. However, the residues defining this β-turn have not been well explored in the previous studies.

So, in order to optimize this mini-protein, variability was introduced to four positions of this β-hairpin. This loop contains three cysteines which are vital to the correct folding of the mini-protein and as a result can not be mutated. As CD4 C" β-strand in complex with gp120, the second β-strand of CD4M33 mainly establishes interactions with β15 strand of gp120 through main-chain atoms. These residues were therefore not modified but rather the top of the loop was explored introducing L- and D-amino acids to position $Gly_{21}$ and $Ser_{22}$ which define the positions i+1 and i+2 of the β-turn. Moreover crystallographic structure of CD4M33 in complex with gp120 (Huang et al., precited), shows that the C' β-strand of CD4M33 is irregular and presents few direct interactions with gp120. Thus, $Lys_{18}$ and $Ala_{20}$ were selected and mutated by L-amino acids in order to modify the mini-protein β-sheet and gain new interactions with gp120.

Finally, in regard to solubility and synthesis yield, the biphenylalanine residue in position 23 was replaced by a phenylalanine in the template used for combinatorial synthesis. The four selected positions were submitted to combinatorial synthesis, incorporating all the amino acids of either (L) configuration or both (L) and (D) configurations except the cysteine (both L- and D-) which was discarded from the diversity to prevent any misfolding during libraries synthesis. The iterative deconvolution method was used to screen the peptide libraries, so that four libraries of, respectively, 19, 19, 34 and 34 sub-libraries were synthesized, to generate 417316 different peptides.

b) Combinatorial Synthesis and Selection

A combinatorial deconvolution strategy was iteratively used to study the four screened positions (a.a.: 18, 20, 21 and 22). It involved a series of 4 libraries comprising mixtures in which the identity of an amino acid at a given position was known. At the remaining positions all combinations of amino acids were incorporated. This procedure is illustrated in FIG. 2. To screen the first position 18 in CD4M33, 19 sub-libraries, names B1A to B1Y, introducing a defined L-amino acid (except cysteine as previously mentioned) at this position were synthesized with an equimolar combination of 19 (L)-aa×34× 34 (L).(D)-aa at position 20, 21 and 22 respectively. Each statistical pool containing 21964 theoretical peptides was achieved by the split-and-combine procedure, one of the most elegant and popular combinatorial strategy, which allows by SPPS chemistry a high statistical sampling of all possible combinations of the 20 natural amino-acid building blocks (Dooley et al., Science, 1994, 266, 2019-2022; Houghten et al., Nature, 1991, 354, 84-86).

Each 19 sub-libraries were then evaluated in terms of quality and homogeneity of synthesis. After cleavage of the resin-bound libraries, four controls were performed: folding monitoring by RP-HPLC, quantitative amino acid composition, circular dichroism and mass spectrum. All those analyses permitted to validate or not the conformity of the library. Typically, the first synthesis of the combinatorial library at position 18 gave evidence that a large quantity of truncated peptides, highlighted by the systematic capping steps, were generated during the synthesis process. Prior to re-generating the entire first library, the synthesis protocol was optimized using first an ABI-433 synthesizer which provides continuous UV-monitoring of the deprotection steps. This analysis revealed the necessity of a double coupling after $Gly_{17}$ to maintain a correct yield. The protocol was also refined by several parallel peptide syntheses on an ACT-357 multi-synthesizer. After the synthesis of an entire library at position 18 including all the improvements, a new control of conformity was processed. That time, RP-HPLC showed a retention time shift of the main peak ensuring that the disulfide bridges were correctly oxidized. Analyzes by MALDI-TOF confirm the presence of the mass pattern at the desired mass. CD spectra were indicative of a global correct folding similar to the CD spectrum of CD4M33 (FIG. 3).

Figure 4:
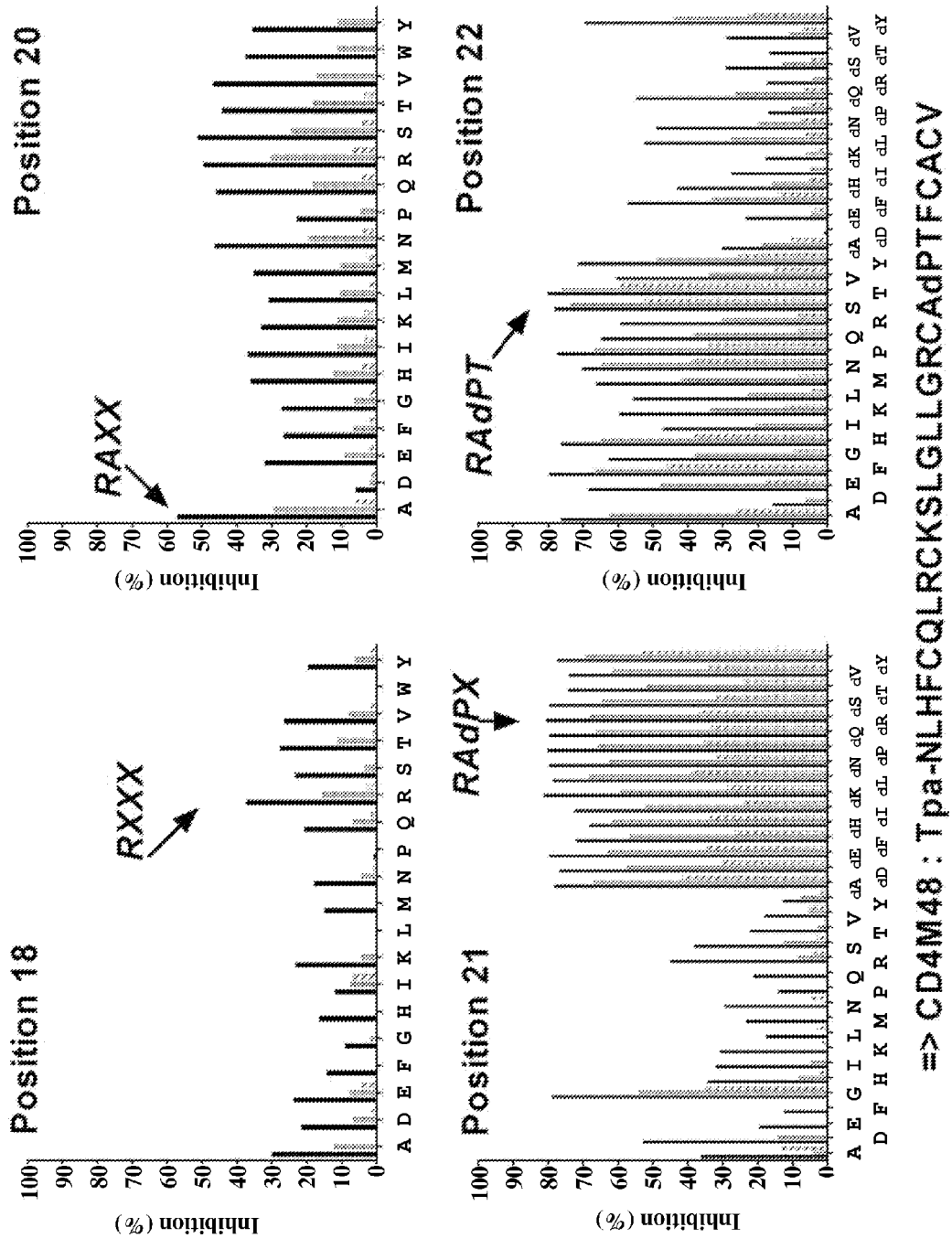
FIG. 4 illustrates the screening of the peptide libraries by fluorescence polarization assay. Inhibition of CD4M33-F (1 nM) binding to $gp120_{HxB2}$ (12.5 nM) of libraries B1, B2, B3 and B4, measured by fluorescence anisotropy at respectively position 18, 20, 21 and 22 in CD4M33. All results are given as the percentage of inhibition of CD4M33-F or sCD4 binding, as a mean of duplicate. Each sub-library is tested at three concentrations: $10^{-6}$ (black), $10^{-7}$ (grey) and $10^{-8}$ M (stripes). Choice of selected residue in each position is indicated by an arrow. X represents an equimolar mixture of (L) amino acids at position 20 and of (L).(D) a.a. at position 21 and 22.
Figure 5:
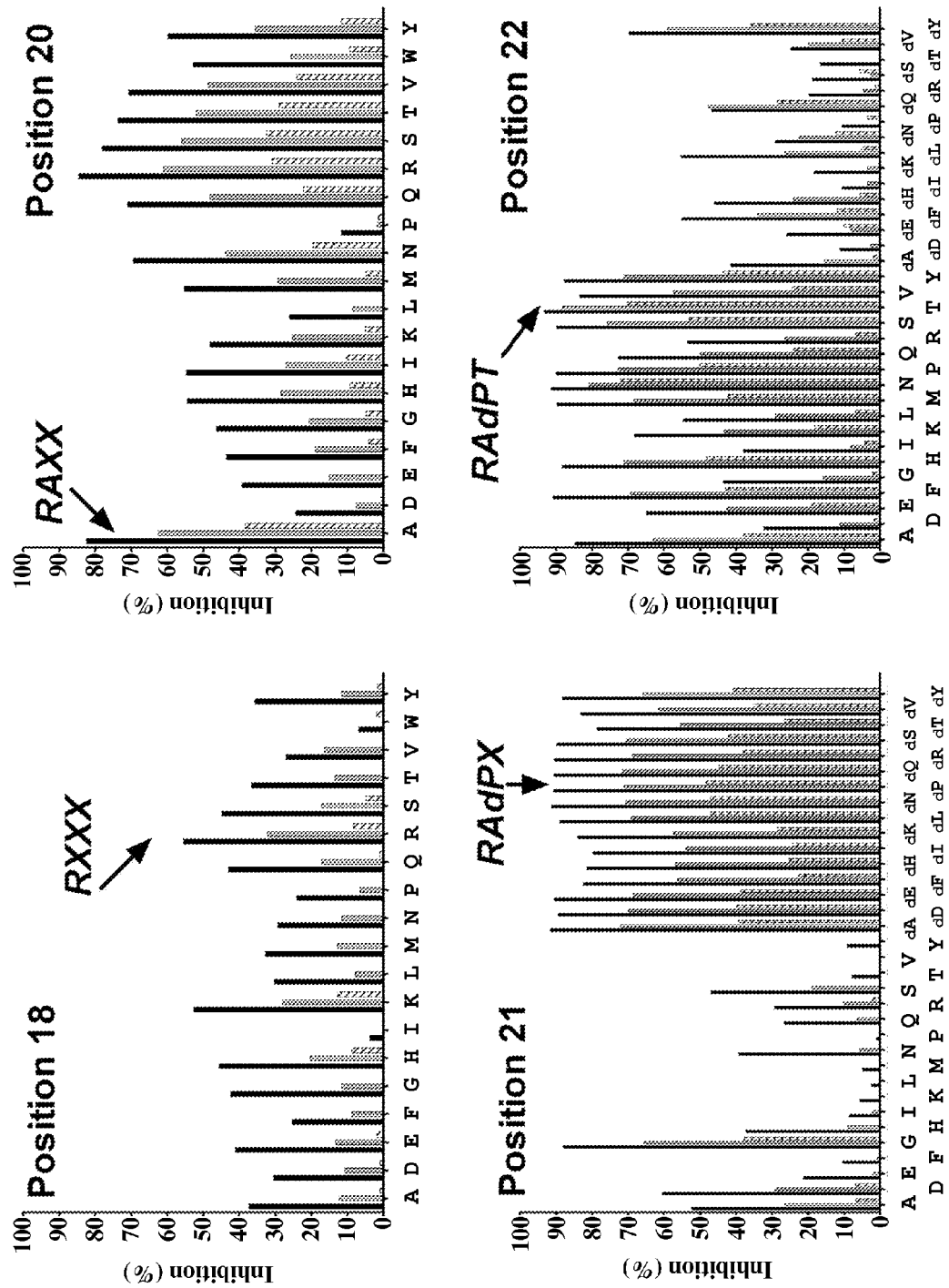
FIG. 5 illustrates the screening of the peptide libraries by competitive ELISA. Inhibition of sCD4 binding to $gp120_{HxB2}$ measured by ELISA of libraries B1, B2, B3 and B4, at respectively position 18, 20, 21 and 22 in CD4M33. All results are given as the percentage of inhibition of sCD4 binding, as a mean of duplicate. Each sub-library is tested at three concentrations: $10^{-6}$ (black), $10^{-7}$ (grey) and $10^{-8}$ M (stripes). Choice of selected residue in each position is indicated by an arrow. X represents an equimolar mixture of (L) amino acids at position 20 and of (L).(D) a.a. at position 21 and 22.
Figure 6:
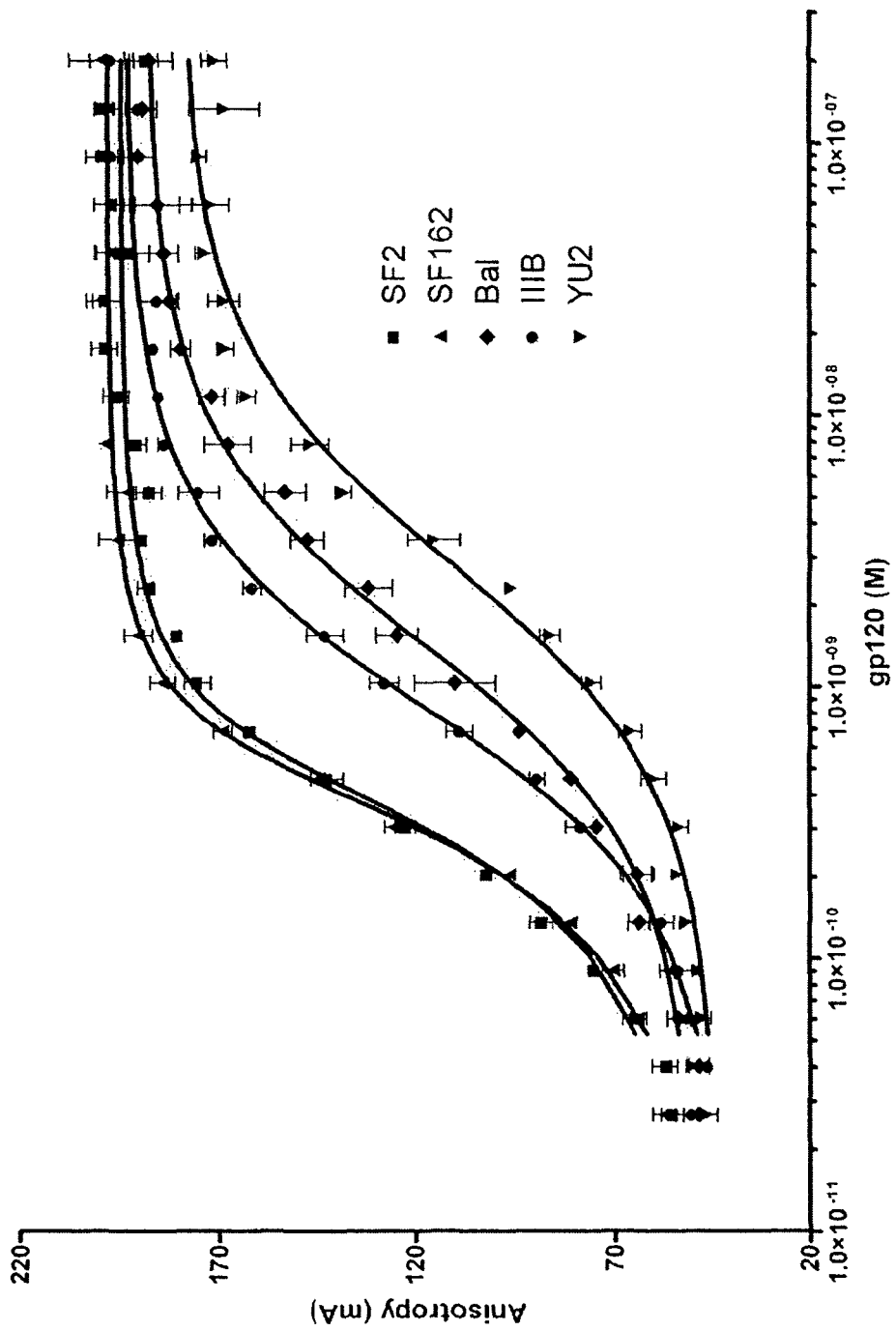
FIG. 6 illustrates the CD4M47-F titration against several gp120 envelopes measured by fluorescence anisotropy. CD4M47-F was used at 0.5 nM. Both X4-tropic (■ SF2, ● IIIB) and R5-tropic (▲ SF162, ♦ Bal, ▼ YU2) gp120 were used.

Concentrations being normalized by quantitative amino acid composition, each sub-library of the first library was tested at three different concentrations ($10^{-6}$, $10^{-7}$ and $10^{-8}$ M) for the inhibition of gp120 binding to CD4 by two different biochemical tests (FIGS. 4 and 5: position 18). Both chosen tests, ELISA and fluorescence anisotropy competition assay, are based on different physical properties (one relying on molecule adsorption and liquid-solid interface, the other on light depolarization and solution equilibrium). In both tests, inhibition at $10^{-8}$ M was low and not significant. On the other hand, with both methods sub-library B1R showed a better activity at $10^{-6}$ and $10^{-7}$ M, followed by B1A in fluorescence anisotropy and B1K and B1H in ELISA. Position 18 was finally fixed as an arginine, whereas the wild-type residue was a lysine. Gp120 appears unable to change its conformation bound to a mini-protein bearing small side-chains at this position, while longer ones may interact with $Ala_{281}$ through water bridges. The remaining positions were then sequentially identified through an iterative procedure of (re)synthesis and screening, as depicted in FIG. 2.

Figure 7:
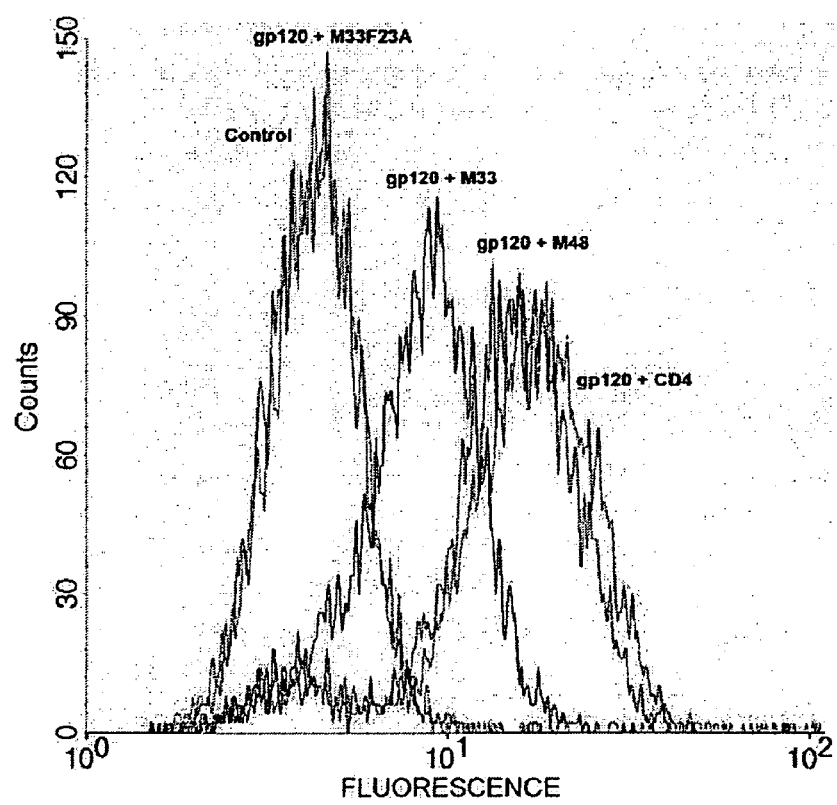
FIG. 7 illustrates the FACS analysis of the binding of recombinant envelope gp120 to $CCR5^+$-CHO cells in absence or in presence of various CD4-mimics, in comparison with soluble CD4.

Thus, a second peptide library consisting of 19 sub-libraries of 1156 compounds each (B2A to B2Y), with a fixed arginine at position 18 and a defined L-amino acid at position 20 was generated. After validation with the four conformity tests, peptide biological activities were measured by ELISA and fluorescence anisotropy (FIGS. 4 and 5: position 20). B2A and B2R rather equivalent at $10^{-7}$ and $10^{-8}$ M presented the best inhibitory activities by fluorescence anisotropy, followed by that of sub-library B2S. However, at a concentration of $10^{-6}$ M, sub-library B2A presented a slightly better activity than B2R. Likewise, B2R and B2A showed identical activity by ELISA at $10^{-6}$ and $10^{-7}$ M, while B2A activity was significantly higher at $10^{-8}$ M. Consequently, position 20 was fixed as an alanine, corresponding to the original amino acid. However, sub-library B2A was only slightly more active than B2R. This position at the beginning of the β-hairpin plays a critical structural role: its main-chain atoms establish hydrogen bonds with backbone atoms of residue 23 and hence stabilize the β-turn. Interactions that could be gained between residue 20 and gp120 seem to be counterbalanced by the destabilization of the turn due to steric clashes, limiting clear selection of new amino acids at this position.

Then a third combinatorial library including 34 sub-libraries of 34 different mini-proteins each (B3A to B3dY) with a fixeD-amino acid of either L- or D-configuration at position 21 was synthesized and tested (FIGS. 4 and 5: position 21). A pronounced difference appeared between sub-libraries containing at position 21 amino acids of L-configuration and those containing amino acids of D-configuration. A clear preference was shown for residues of D-configuration and to a lesser extend for glycine (which is achiral). The selection at this position of a whole family of amino acids suggested a purely structural effect of the mutation, which was confirmed by the small difference in activity between the different sub-libraries with a D-amino acid. The type II' β-turn seemed to be the most favourable turn for the activity of the mini-proteins. Based on those results, and to emphasize the structural aspect of this mutation, (D)-Proline was chosen for position 21.

The fourth and last library was a parallel synthesis of 34 different peptides with a defined (L).(D) amino acid at position 22 (B4A to B4dY). Each individual mini-protein was then tested at the same three concentrations ($10^{-6}$, $10^{-7}$ and $10^{-8}$ M) for their ability to inhibit CD4 binding to gp120 by ELISA and CD4M33-F1 binding to gp120 by fluorescence anisotropy (FIGS. 4 and 5: position 22). Position 21 being fixed as a (D)-Proline, sub-libraries of the last peptide library are divided in two groups, active amino acids of configuration L and inactive (D)-amino acids. A single peptide of D-configuration B4dY had a good activity. Among the mini-proteins containing an L-amino acid, B4T, B4S and B4N presented the best inhibition. This negative selection of (D)-residues corresponds to a structural preference. Two consecutive amino acids of the same configuration result in destabilizing the type II' β-hairpin. Moreover, steric hindrance strongly selects small amino acids, particularly polar ones such as Threonine, Serine and Asparagine which can interact with the backbone oxygen of Methionine 426 through hydrogen bonds. B4T being the best mini-CD4, position 22 was thus fixed as a threonine. The final selected sequence is shown at the bottom of FIG. 4.

c) Characterization of Optimized Compound Binding to gp120.

The optimized compound named CD4M48, and its CD4M47 homologue presenting a biphenyl instead of the phenyl moiety at position 23 were individually synthesized. They were tested in competitive polarization against CD4M33-F1 as described in Stricher et al (precited), showing an increased efficiency compared to CD4M33 and sCD4. Moreover, in order to have more relevant thermodynamic dissociation constants in solution, both peptides were labeled with the optimized quantic fluorescence yield Alexa-488 probe. Fluorescence anisotropy measurements were based on the assessment of the rotational motions of species. Whereas the CD4-mimic tumbles very fast in solution randomizing excited molecules, once it binds to gp120 envelopes, the excited mini-protein stays aligned during the process of emission and as a result, emitted light is polarized. Several gp120 isolates, from dual-tropic SF2, X4-tropic IIIB or R5-tropic Bal, SF162, YU2 were titrated with both 0.5 nM of CD4M48 and CD4M47 labeled peptides (FIG. 6). Apparent Kds, determined by fitting experimental data to equation (1) using non-linear regression program are reported in Table I.

TABLE I

Dissociation constants of Alexa labeled mini-proteins CD4M33, CD4M48 and CD4M47.

| gp120 | CD4M33 (Kd, nM) | CD4M48 (Kd, nM) | CD4M47 (Kd, nM) |
|---|---|---|---|
| SF2 | 0.759 ± 0.03 | 0.708 ± 0.07 | 0.0843 ± 0.01 |
| SF162 | 0.833 ± 0.04 | 0.138 ± 0.0016 | 0.0675 ± 0.007 |
| Bal | 6.36 ± 0.26 | 5.46 ± 0.23 | 1.22 ± 0.07 |
| IIIB | 3.81 ± 0.15 | 0.982 ± 0.08 | 0.589 ± 0.03 |
| YU2 | 15.2 ± 0.76 | 4.08 ± 0.2 | 2.66 ± 0.16 |

Compared to the results already obtained with CD4M33 (Martin et al., precited), the affinities of CD4M48-F1 are about a factor of 1.1 to 6.1 smaller. CD4M47-F1 presented substantially better affinities, giving an improvement of 5.2- to 12.3-fold depending on isolates. The biphenylalanine in position 23 led to a 3 fold gain, consistent with the previously observed difference between CD4M33 and its [$Phe^{23}$]M33 mutant (Huang et al., Structure, 2005, 13, 755-768).

CD4M33 is able to induce a CD4-like conformational change in gp120 (Martin et al., precited). However, this visualization was only carried out using indirect surface plasmon resonance analysis of gp120 binding to CD4-induced antibodies such as 17b, X5 and 48D immobilized on a sensorchip. Both CD4M47 and CD4M48 presented the same ability to unmask conserved co-receptor neutralization epitopes as the prototype CD4M33. A first experiment showed that gp120 incubated with Alexa 488-labeled CD4M48 could bind directly to $CCR5^+$-CHO cells. In order to give evidence that the full range of CD4-like changes occurs, the amount of gp120 bound to CCR5+cell lines in absence or in presence of CD4 or CD4M48, was compared. CD4M48 was shown to induce the same recognizing of $CCR5^+$-CHO cells as CD4 in presence of gp120. Besides, CD4M33-F23A, in which the critical residue Bip23 was substituted by an alanine, once incubated with gp120 was confirmed as a specific control unable to bind to $CCR5^+$-CHO. Binding ability to CCR5 was well correlated to the affinity towards gp120. Indeed, an intermediate fluorescence response of CD4M33 which presented a higher affinity to gp120 compared to CD4M48 was observed (FIG. 7). Thus, CD4M48 is able to stabilize the CD4-bound conformation of gp120. Indeed, CD4M48, once bound to gp120, can increase gp120 affinity for chemokine receptors, to a level comparable to that observed with CD4, as shown by direct FACS binding assays to CCR5+ cells. This result stresses that the strategy of cross-linking this mini-protein with gp120 so as to produce immunogenic complex could offer the full range of envelope conformational changes, condition sine qua non to elicit neutralizing antibodies.

d) CD4M48 Structure in Complex with HIV-1 core gp120

Both CD4M48 and CD4M47 peptides were co-crystallized in ternary complex with core gp120 from the primary HIV-1 isolate YU2 and the antigen binding fragment (Fab) of 17b antibody. The structure was solved by using molecular replacement with the homologue CD4 complex. The structure of the newly determined CD4M48/gp120/17b complex is quite similar to the previous CD4M33 one (Huang et al., precited). Nevertheless, analysis of contact surfaces revealed some differences. For mimetic residues 18, 20, 21, in each case, combinatorial optimization resulted in an enhancement in the contact surface. For residue 18, the increase was roughly 20 Å$^2$, and for residues 21 and 22, the increase roughly 10 Å$^2$. Thus, good correlation was found between affinity and increase in contact surface area between mimetic and gp120.

e) Neutralization Assay

To analyze the inhibitory activity of the new compounds, both CD4M47 and CD4M48 were compared to their parent molecules (respectively CD4M33 and [Phe$^{23}$]M33) and sCD4 in neutralization cell line assay. The susceptibility of various envelope clones to be inhibited by CD4-mimic peptides was analyzed using a broadly sensitive HIV-entry assay able to give quantified infection within a single cycle of replication (Salzwedel et al., J. Virol., 2000, 74, 326-333). Using JC53BL-13 indicator cell line, HIV neutralization escapes were evaluated with various isolate envelopes, not only of HIV-1 type but also of HIV-2 and SIV types (Wei et al., Nature, 2003, 422, 307-312). The results are summarized in Table II.

TABLE II

Comparison of the antiviral activities between sCD4, CD4M33, [Phe$^{23}$]M33, CD4M47 and CD4M48.

| Virus | Species | sCD4 (Kd, nM) | [Phe23]M33 (Kd, nM) | CD4M33 (Kd, nM) | CD4M48 (Kd, nM) | CD4M47 (Kd, nM) |
|---|---|---|---|---|---|---|
| NL4.3 env° | HIV-1 groupM | 2.0 | 13.0 | 5.0 | 4.0 | 3.0 |
| YU-2 env° | HIV-1 groupM | 8.0 | 1023.0 | 207.0 | 149.0 | 64.0 |
| MN-8° | HIV-1 groupM | 0.5 | 85.0 | 34.0 | 15.0 | 11.0 |
| MN-25° | HIV-1 groupM | 36.0 | 3583.0 | 348.0 | 316.0 | 153.0 |
| WEAU 16-8M° | HIV-1 groupM | 1.0 | 133.0 | 85.0 | 47.0 | 64.0 |
| SUMAd736-68° | HIV-1 groupM | 2.0 | 28.0 | 4.0 | 7.0 | 3.0 |
| SUMAd736-73° | HIV-1 groupM | 56.0 | 8486.0 | 478.0 | 948.0 | 374.0 |
| BaL* | HIV-1 groupM | ND | 203.0 | 116.0 | 33.0 | 27.0 |
| IIIB* | HIV-1 groupM | ND | 258.0 | 12.0 | 7.0 | 8.0 |
| 6195* | HIV-1 groupM | ND | 209.0 | 16.0 | 13.0 | 7.0 |
| US714* | HIV-1 groupM | ND | 745.0 | 180.0 | 48.0 | 37.0 |
| GAB-1 fl° | SIVcpz (P.t.t.) | 4.0 | 351.0 | 340.0 | 69.0 | 152.0 |
| GAB-2 62 fl° | SIVcpz (P.t.t.) | 16.0 | 1018.0 | 403.0 | 292.0 | 234.0 |

°tested by HIV entry assay in PM1 cell line
*tested by modified HIV entry assay in JC53BL-13 cell line Sensitivity to neutralization by mini-proteins varied substantially depending on HIV strains, but remained lower than for CD4. Stabilizing of the type II' β-turn in CD4M48 leads to a significant increase (up to 10 fold) of its neutralization potency of HIV infection, compared to its parent molecule [Phe$^{23}$]M33. The addition of a biphenyl moiety at position 23 in CD4M47 peptide led to more subtle differences, depending mainly on the isolates. For highly sensitive isolates from group M such as NL4.3, YU2, MN-8, MN-25, the biphenyl moiety always provided an improvement in efficiency compared to phenyl group. In contrast, for viruses evolutionarily far away from clade B, like SIVcpz, the phenyl group appeared to induce more potency than the biphenyl group. Overall, the benefit of incorporating a biphenylalanine in position 23 observed in CD4M33 compared to [Phe$^{23}$]M33 was greatly decreased when included in CD4M47 peptide compared to CD4M48. The biphenyl is a rigid moiety which could accommodate itself to the rather flexible β-turn of our previous template in CD4M33. Stabilizing the β-turn impedes the adaptation of the mini-protein to this rigid sidechain, which could explain the small increase of neutralization activity after mutating position 23.

EXAMPLE 2

Optimization of the Filling of Phe-43 Binding Pocket

Figure 8:
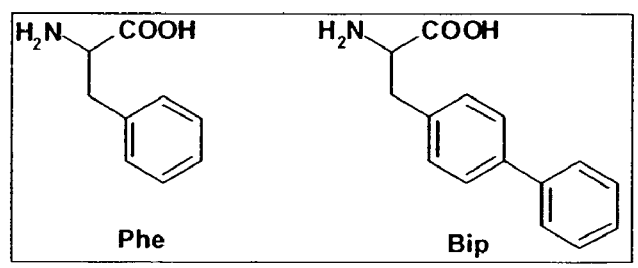
FIG. 8 represents phenylalanine (Phe or F) and Biphenylalanine (Bip) structure.
Figure 9:
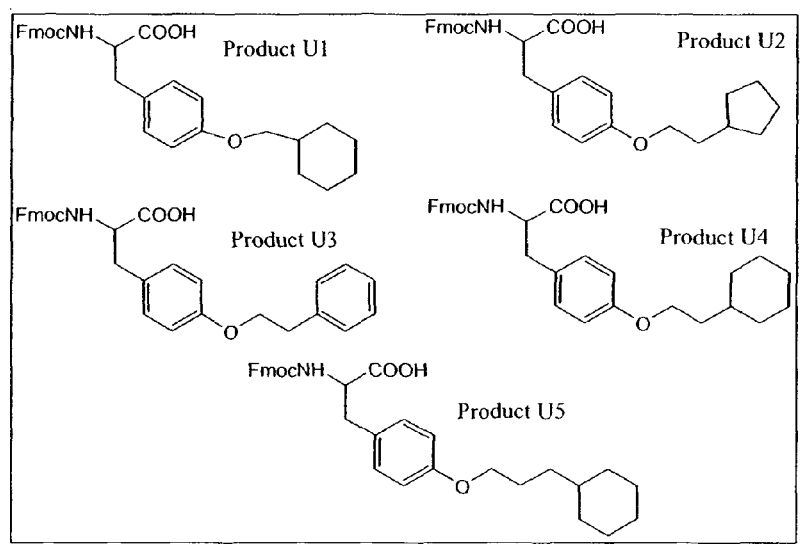
FIG. 9 represents the phenylalanine derivatives with para [c-alkyl or c-aryl alcoxy chain] for replacing the Phe43 residue in CD4M48. U1: Fmoc-Phe(para-[c-hexylmethoxy])—OH. U2: Fmoc-Phe(para-[c-pentylethoxy])—OH. U3: Fmoc-Phe(para-[phenyl-ethoxy])—OH. U4: Fmoc-Phe(para-[c-hexyl-ethoxy])—OH. U5: Fmoc-Phe(para-[c-hexylpropanoxy])—OH.
Figure 10:
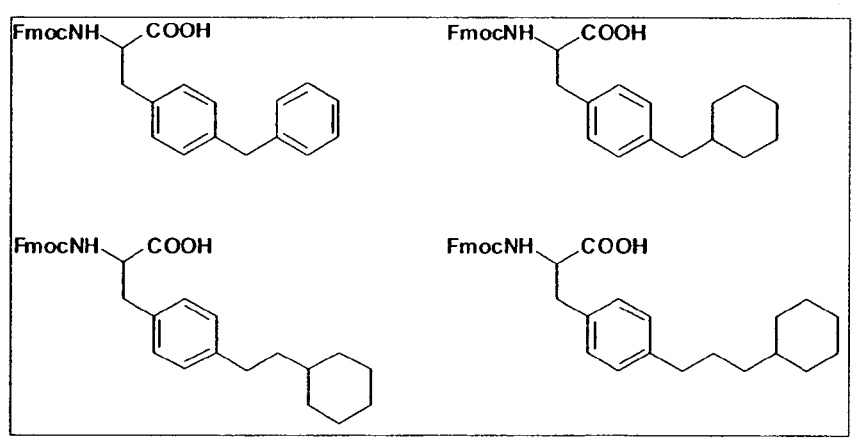
FIG. 10 represents the phenylalanine derivatives with para [c-alkyl or c-aryl alkyl chain] for replacing the Phe43 residue in CD4M48.

CD4M33 has been shown to present optimal interactions with gp120 and bind to the viral particles and to the diverse HIV-1 envelopes with CD4-like affinity (Martin et al., precited). In this CD4 mimic, Phe23 is replaced by a biphenylalanine (Bip) residue, ie a phenylalanine with an additional hydrophobic phenyl moiety in the para position, FIG. 8), with the aim of increasing the interactions with the gp120 apolar "Phe43 cavity". In order to further increase the interactions with gp120, new peptidyl CD4 mimics, where the Phe23 is replaced by some non-natural phenylalanine derivatives, were synthesized. This was achieved by synthesizing the non-natural phenylalanine derivatives which were then incorporated in the peptide of interest. Preliminary studies showed that the replacement of Phe23 by para-methylphenylalanine or by para-methoxyphenylalanine reduces the M33-gp120 affinity, while Phe23 can be replaced by β-naphtylalanine (similar affinity). Therefore some phenylalanine derivatives with para[c-alkyl or c-aryl alkyl or alcoxy chain] were studied (FIGS. 9 and 10).

1) Synthesis of Phenylalanine Derivatives with para[c-alkyl or c-aryl alcoxy Chain]

a) Experimental Procedures

The synthetic route described by A. D. Morley (Tetrahedron Lett., 2000, 41, 7405-7408) was used, in order to produce more diverse compounds. This route allows the preparation of an ether series derived from the tyrosine amino acid by using the Mitsunobu reaction by solid phase synthesis (FIGS. 11A and B).

The first step (a) is the bis-protection of tyrosine amino acid using allyl chloroformate, as described in Stevens, C. M. and Watanabe, R., J. Am. Chem. Soc., 1950, 72, 725-727 (FIG. 11A). Tyrosine (n=0.03 mol, m=5.44 g) is dissolved in 15 ml of 4N sodium hydroxide and treated, when cold, with 7.02 ml (2.2 equiv.) of allyl chloroformate and additional 15 ml of 4N sodium hydroxide. After treatment and purification, O,N-dicarboallyloxy-L-tyrosine is obtained in 89% yield (Litt. 91%) as a crystalline derivative.

Then, in step (b), the protected amino-acid is immobilised on Wang (p-benzyl-oxybenzyl alcohol) resin (ALDRICH, 1.82 mmol/g) using 3 equivalent each of O,N-dicarboallyloxy-L-tyrosine and diisopropylcarbodiimide plus 0.1 equiv. of dimethylaminopyridine in DMF. Loading is estimated by cleavage and weight analysis of little weighed samples of resin. Loading of 0.993 mmol/g (88% theoretical) is obtained.

In step (c), the carbonate protecting group is selectively removed under mild conditions, as described in A. D. Morley (precited; FIG. 11A). Treatment of bis-protected tyrosine resin with a solution of 20% piperidine in DMF for 24 hours resulted in complete and selective removal of the carbonate, these conditions are mild enough to avoid detachment of the template from the solid support and under which allylcarbamate is stable. The reaction occurs quantitatively (estimated by cleavage): loading of 1.08 mmol/g is obtained.

This selective removal of the phenolic protecting group generates an intermediate that is suitable for synthesizing an ether library by using the Mitsunobu reaction (FIG. 11B). Mitsunobu reaction (step (d)) is carried out in a 1:1 mixture of DCM/THF at room temperature for 24 h with alcohol, $PPh_3$ and isopropylazodicarboxylate (5 equiv. each), in double coupling (double coupling increase the yield of reaction, but even after two Mitsunobu reactions, the best yield obtained is 80%, the remaining product is the phenol which did not react).

Then, the allyloxycarbonyl group can easily be removed (step (e)) to reveal the primary amine under mild conditions, under which the majority of other functional groups is inert. N-alloc deprotection is activated with $Pd(PPh_3)_4$ (0.5 equiv.), in THF/DMSO/0.5M HCl/morpholine:20/20/10/1 ratio, at room temperature for 24 h with quantitatively yield (caution: it is essential to wash the resin with 0.1M solution of diethyldithiocarbamic acid, sodium salt hydrate in addition to standard washing protocols in order to remove all traces of catalyst from the resin).

In step (f), a Fmoc group is introduced protecting the resulting amine and the synthesized amino acid is cleaved from the solid support in acidic conditions. The resulting amine is protected by a Fmoc group with 9-fluorenyl-methylchloroformate (3 equiv.) and diisopropylethylamine (4 equiv.) in DCM at room temperature for 24 h. The last step (g), the deprotection/cleavage is carried out in a 3:7 mixture of TFA:DCM at room temperature for 1 h. After extraction and filtration (on silica gel eluted by DCM/MeOH, 98:2), the non-natural amino acids are obtained with suitable protective groups for peptide synthesis in Fmoc conditions. Each of the non-natural amino acid (FIG. 9) was used for synthesis of the CD4M48 peptido-mimetics replacing the Phe23 residue. Their introduction was made in double coupling, by using 5 molar equiv.

b) Results

The compounds U1 to U5 were synthesized (FIG. 9).

Fmoc-Phe(para-[c-hexylmethoxy])-OH (Product U1)

From 5.44 g (n=0.03 mol) of tyrosine, 9.35 g (0.027 mol) of product 1 are obtained (89% yield). All protected tyrosine is involved with 4.9 g (1.82 mmol/g, 9 mmol) of Wang resin and 7.8 g of a 0.993 mmol/g preloaded resin 2 are obtained. After deprotection of the carbonate, we estimated a 100% yield so 7.15 g of a 1.08 mmol/g loaded resin 3. With 3 g of this resin (3.24 mmol), cyclohexylmethanol (5 equiv.), TPP (5 equiv.) and DIAD (5 equiv.), in double coupling, the Mitsunobu reaction gives 3.25 g of a 0.78 mmol/g loaded resin 4. After steps of N-alloc deprotection, N-Fmoc protection and cleavage, 657 mg (1.32 mmol) of Fmoc-Phe(para-[c-hexylmethoxy])—OH are obtained.

Fmoc-Phe(para-[c-hexylmethoxy])—OH (product U1)

$^1$H NMR ($CDCl_3$) δ 0.96-1.10 and 1.14-1.37 (2m, 8H, 4 $CH_2$ c-hexyl), 1.63-1.91 (m, 3H, 1 CH and 1 $CH_2$ c-hexyl), 3.11 (qd, 2H, $CH_2β$, J=15.3 Hz, J=5.4 Hz), 3.70 (d, 2H, O$CH_2$, c-hexyl, J=6.2 Hz), 4.21 (t, 1H, CH(Fmoc), J=7.1 Hz), 4.37 (dd, 1H, $NHCOOCH_2$, J=9.8 Hz, J=6.6 Hz), 4.45 (dd, 1H, $NHCOOCH_2$, J=10.5 Hz, J=7.1 Hz), 4.67 (td, 1H, $CH_2α$, J=6.0 Hz, J=5.9 Hz), 5.17 (d, 1H, NH, J=8.1 Hz), 6.81 (d, 2H, 2CH Ph, J=8.1 Hz), 7.04 (d, 2H, 2CH Ph, J=8.1 Hz), 7.31 (t, 2H, 2CH Fmoc, J=7.4 Hz), 7.41 (t, 2H, 2CH Fmoc, J=7.4 Hz), 7.55 (t, 2H, 2CH Fmoc, J=6.2 Hz), 7.76 (t, 2H, 2CH Fmoc, J=7.3 Hz).

$^{13}$C NMR ($CDCl_3$) δ 25.8 (C3, C3', c-hexyl), 26.5 (C4, c-hexyl), 29.9 (C2, C2', c-hexyl), 30.9 (C1, c-hexyl), 37.7 (CH Fmoc), 47.1 ($CH_2β$), 63.3 ($CH_2α$), 66.9 (c-hexyl$CH_2$O), 73.4 ($NHCOOCH_2$, 114.6 (2 CH phenyl), 120.0 (2 CH Fmoc), 125.0 (Cq, phenyl), 127.0 (4 CH Fmoc), 127.7 (2 CH Fmoc and 2 CH Phenyl), 130.3 (2 Cq Fmoc), 141.2 (2 Cq Fmoc), 155.7 (Cq Phenyl), 158.5 (NHCOO), 175.8 (COOH).

SM(ES): $(M+H)^+$ m/z=499.2. Anal. C31H33NO5

Fmoc-Phe(para-[c-pentylethoxy])-OH (product U2)

SM(ES) $(M+H)^+$ m/z=499.2. Anal. C31H33NO5

Fmoc-Phe(para-[phenyl-ethoxy])-OH (Product U3)

SM(ES) $(M+H)^+$ m/z=507.2. Anal. C32H29NO5

Fmoc-Phe(para-[c-hexylethoxy])-OH (Product U4)

SM(ES): $(M+H)^+$ m/z=513.2. Anal. C32H35NO5

Fmoc-Phe(para-[c-hexylpropanoxy])—OH (Product U5)

SM(ES): (M+H)⁺ m/z=527.3 Anal. C33H37NO5

2) Determination of Binding Affinities to gp120
a) Experimental Procedures

The experimental procedures are as described in Example 1.

b) Results

Figure 12:
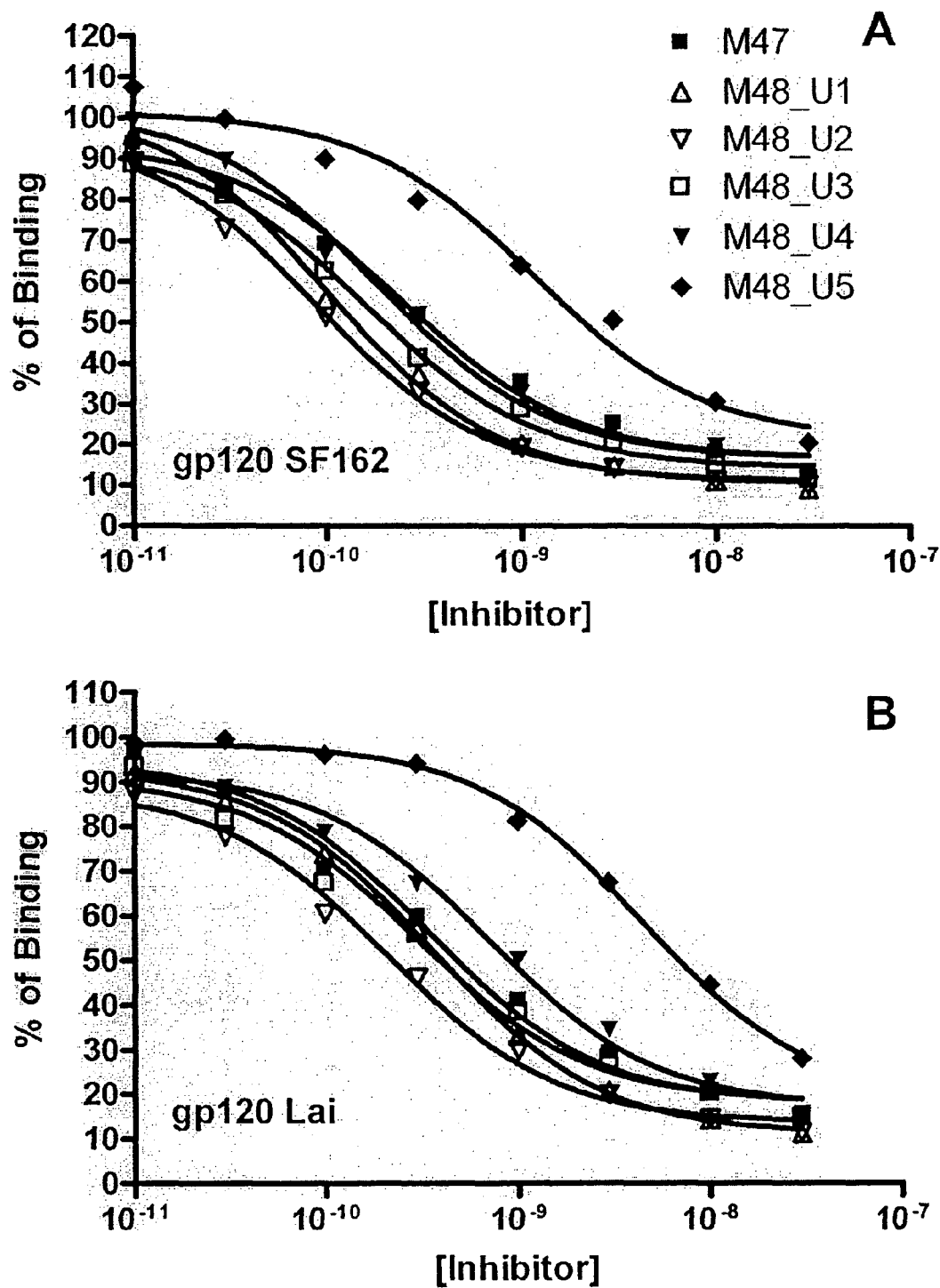
FIG. 12 illustrates the inhibition of sCD4 binding to both gp120LAI and gp120SF162 measured by ELISA. CD4M48_U1:△, CD4M48_U2: ▽, CD4M48_U3: □, CD4M48_U4: ▼, CD4M48_U5: ♦ are compared to CD4M47 (CD4M48-Bip).

The ability of the CD4M48 peptides having different Phe derivatives in position 23 to inhibit gp120 binding to CD4 was assayed by competitive ELISA, by comparison with CD4M47 (CD4M48Bip23). The incorporation of c-pentylethoxy- in para position of residue Phenylalanine-23 gives the highest affinity to both gp120Lai and gp120SF162 with an up-to-three fold enhanced affinity compared to CD4M47 (FIG. 12 and Table III).

HIV Single Cycle Pseudovirus Assay

Fifty microliters of HIV pseudovirus were pre-incubated with 50 µl of a dilution series of a CD4 miniprotein or reference compound. After 15 minutes, 100 µl of GHOST target cells (AIDS REFERENCE AND REAGENT PROGRAM; $1.2 \times 10^5$ cells/ml) expressing CD4 and either of the HIV co-receptors CCR5 or CXCR4 were added to the 96-well cups containing the pre-treated pseudovirus. The GHOST cells were lysed 48 h post-infection by addition of the luciferin substrate (SteadyLite HTS, PERKIN ELMER LIFE SCIENCES). The resulting light signal, expressed as relative lights units (RLU), was quantified in a luminometer (Top Count™, CANBERRA-PACKARD). The percentage compound-mediated inhibition of viral infection, as compared to untreated controls, was plotted against the concentration of compound and linear regression analysis was done to calculate the 50% effective concentration (EC50).

TABLE III

Affinity* of the CD4M48 derivatives by comparison with CD4M47 (M48Bip23)

| | CD4M47 | CD4M48_U1 | CD4M48_U2 | CD4M48_U3 | CD4M48_U4 | CD4M48_U5 |
|---|---|---|---|---|---|---|
| Gp120_Lai | 0.35 | 0.36 | 0.21 | 0.3 | 0.7 | 4.49 |
| Gp120_SF162 | 0.25 | 0.11 | 0.09 | 0.17 | 0.19 | 1.19 |

*IC50 (nM)

Figure 13:
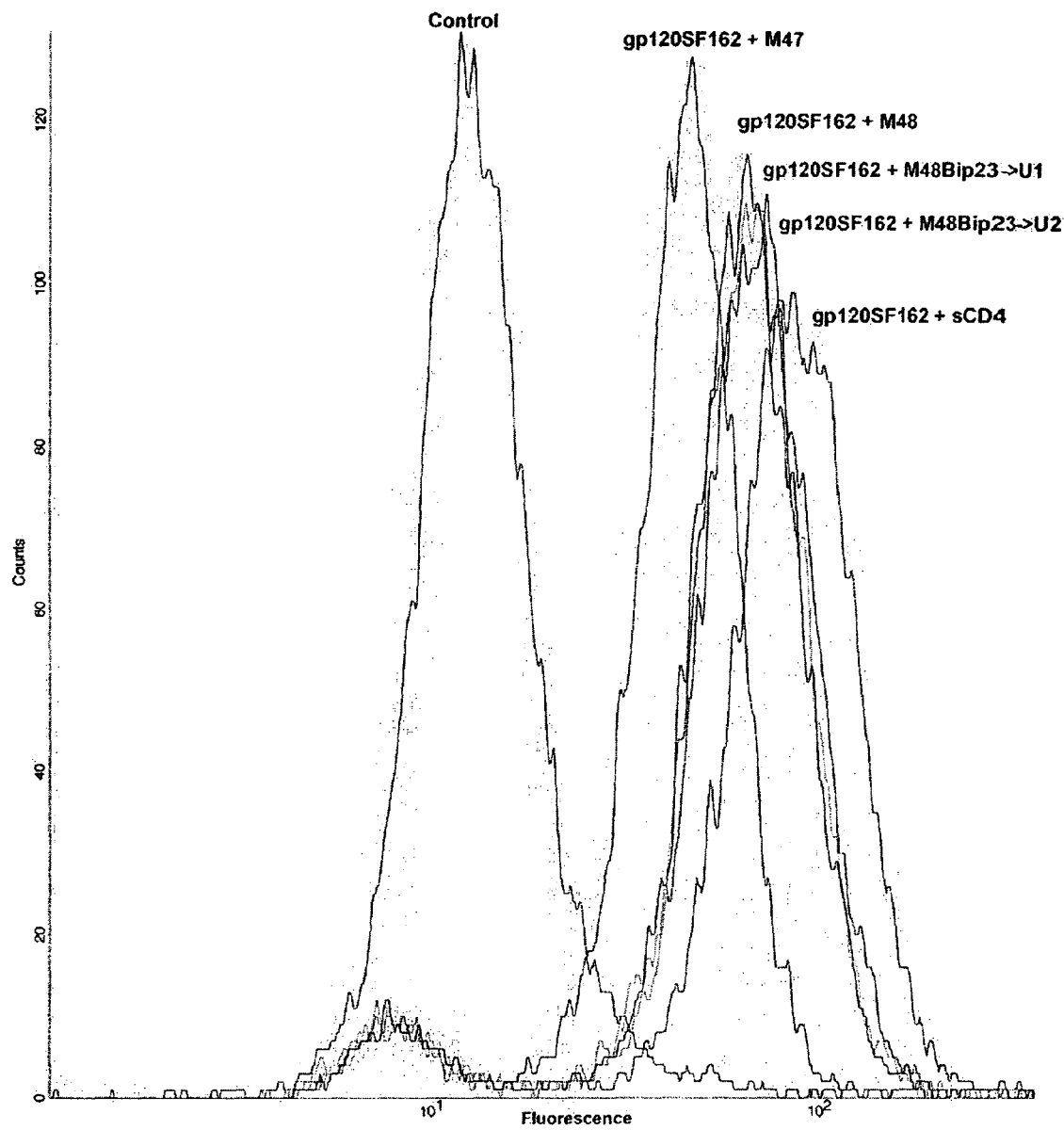
FIG. 13 illustrates the FACS analysis of the binding of recombinant envelope gp120 to $CCR5^+$-CHO cells in absence or in presence of various CD4-mimics in comparison with soluble CD4.

Gp120 in complex with these compounds was able to bind to CCR5+ cells (FIG. 13). As compared to CD4M48, CD4M48_U1 and CD4M48_U2 showed a better ability to induce the conformational change of gp120.

3) Biological Studies
a) Experimental Procedures
HIV and HIV Derived Pseudoviruses For single-cycle infection experiments, HIV pseudoviruses representative of different HIV-1 subtypes were produced by co-transfection of $2 \times 10^5$ HEK293 (American Type Culture Collection) derived cells expressing the SV40 T antigen (HEK293 T), using the calcium phosphate method (Pro-Fection® mammalian transfection system; PROMEGA). To this end, 1 µg of an HIV-1 env expressing vector under control of a CMV promoter, derived from pcDNA4/TO backbone vector (INVITROGEN) and 400 ng of the HIV-1 genomic vector (pNL4-3.Luc R⁻E⁻; National Institutes of Health AIDS Research and Reference Reagent program; catalogue number 3418), under control of the LTR promoter were used. pNL4-3.Luc R⁻E⁻ contains the whole HIV genome, including a packaging signal, but has a frameshift in the env and vpr genes rendering it non-infectious. Furthermore a luciferase reporter gene replaces the nef gene. After 24 h, the medium was replaced with medium containing 1 mM sodium butyrate (SIGMA-ALDRICH) and the cells were further incubated for an additional 24 h. Afterwards, the supernatant with the pseudovirus was harvested, filtered (Millex 0.45 µm filters, MILLIPORE) and after adding Fetal calf serum (FCS; 10%) stored at −80° C. Pseudoviruses of different HIV-1 subtypes were created, including pseudoviruses derived from the subtype B, CCR5 co-receptor using strains Ba-L and SF162; the subtype B, CXCR4 co-receptor using strains Mn; the subtype C, CCR5 co-receptor using strains VI829, VI1358 and MJ4 and the CRF01_AE, CXCR4 co-receptor using strain CA10-3.

Dendritic cell experiments were preformed with the replication-competent CCR5 co-receptor, using non-syncytium inducing, subtype B HIV-1 strain Ba-L whose infectious titer was determined on cultures of PHA/IL-2 stimulated PBMC.

Dendritic Cells Assay

Monocytes were separated from the buffy-coats of HIV seronegative blood donors by counter-flow elutriation and E-rosetting. They were subsequently differentiated to monocyte-derived dendritic cells (MO-DC) using GM-CSF and IL-4. Fifty microliters of HIV-1 Ba-L (corresponding to a multiplicity of infection (MOI) of $10^{-3}$) were pre-incubated with 50 µl of a dilution series of a CD4 miniprotein or reference compound (TMC120 and sCD4). After 30 minutes, 100 µl of MO-DC were added ($4 \times 10^5$ cells/ml) and incubated for 2 h (37° C., 5% CO$_2$). Afterwards, cells were washed 3 times and autologous CD4+ T cells were added, in the presence of compound. Co-cultures were incubated for 24 h, after which the cells were washed again (3 times) to remove the compound. Cells were incubated during 14 days of primary culture, during which half of the culture medium was refreshed twice weekly, without compound. At day 14, cultures were washed and PHA/IL-2 activated PBMC were added ($2 \times 10^5$ cells/cup) to detect any latent or subliminal infection during a supplementary 14 days of secondary culture. Culture supernatants of primary (day 7 and day 14) and secondary (day 28) cultures were analyzed for the presence of HIV p24 Ag by a monoclonal p24 antibody (HuMab-HIVp24; BIOMARIC NV) enzyme-linked immunosorbant assay (ELISA). The percentage compound-mediated inhibition of viral infection, as compared to untreated controls, was plotted against the concentration of compound and linear regression analysis was done to calculate the 50% effective concentration (EC50). The minimal concentration of compound (Cmin) that blocked the infection below the detection limit of the ELISA (20 pg HIV p24 Ag/ml) was determined in the primary culture supernatants and absence of infection at this concentration of compound was further confirmed by ELISA analysis of the secondary cultures supernatants after day 28.

WST-1 Cytotoxicity Assay

Cytotoxicity of the compounds was evaluated using an enhanced colorimetric MTT-assay, WST-1, according to the manufacturer's instructions (ROCHE). Target cells were either co-cultures of monocyte-derived dendritic cells and allogeneic CD4+ T cells or cultures of ME-180 endocervical cells. Briefly, MO-DC/CD4+ T cell co-cultures or ME-180 cells were incubated for respectively 5 days or 24 hours, in the presence of compound. WST-1 reagent was added on the last day of the (co-)culture. Cellular cytotoxicity was quantified 6 h later by analysis in ELISA. The percentage cell viability, compared to untreated controls, was plotted against the compound concentration and linear regression analysis was done to calculate the 50% cytotoxic concentration (CC50).
b) Results
CD4 Mimetic Miniproteins Show Potent Antiviral Activity Against HIV-1 Pseudovirus Infection The two classes of CD4 mimetic miniproteins were evaluated in the single-cycle HIV-1 SF162 pseudovirus assay. The first group of molecules consisted of the monomeric CD4 miniprotein CD4M33 in comparison with combinatorial optimized CD4M47 and CD4M48 (example 1). The second one was the evaluation of the mimics filling the Phe-43 binding pocket. Whereas M47 and M33 were similarly active at about 20 nM, approximately 4-fold higher activity was found for M48 (EC50: 5 nM) (Table IV). But more strikingly, M48_U1 showed a 36 fold enhancement in terms of antiviral activity (EC50: 0.65 nM). In comparison, M48_U2 and M48_U3 are less efficient.

should be evaluated against viral isolates which predominantly occur in those specific areas. To this end, the activity of the CD4 miniproteins against three CCR5, subtype-C isolates (VI829, VI1358 and MJ4) was evaluated also.

In general, the antiviral activity of most CD4 miniproteins showed a same tendency towards a decrease in EC50 values as was seen with the V1829 isolate. However, the decrease in antiviral activity was less pronounced for the CD4 miniproteins targeting the Phe43 cavity.

Furthermore and importantly, the evaluated compound M48_U1 remained the best and highly active (EC50: 10 nM range) against all the subtype C isolates.

Besides these subtype-C isolates, the activity of the compounds against CA10-3, a circulating recombinant form of subtype A and E which uses the CXCR4 co-receptor, was evaluated also (Table IV). In contrast to the results obtained with the subtype C isolates, potent antiviral activity was found for most CD4 miniproteins, with EC50 values ranging from 8 0 nM for the monomeric M33 miniprotein to 0.3 nM for the M48_U1 derivative. With all HIV-1 subtypes, the M48_U1 miniprotein showed to be more potent than the sCD4 and almost as effective as the Non Nucleosidic Reverse Transcriptase Inhibitor (NN-RTI) TMC120.
CD4 Mimetic Miniproteins Inhibit HIV-1 Ba-L Infection of MO-DC/CD4+ T Cell Co-Cultures.

TABLE IV

Evaluation of the antiviral activity of the M48 derivatives against a selection of HIV-1 pseudovirus isolates.

| Subtype | B | C | | | | CRF01_A/E | B |
|---|---|---|---|---|---|---|---|
| Co-receptor | | R5 | | | | X4 | |
| PV | SF162 | Ba-L | VI829 | VI1358 | MJ4 | CA10-3 | Mn |
| M33 | 21 | 821 | >3415 | >3415 | >3415 | 80 | 1 |
| M47 | 22 | 108 | 1205 | 579 | >3407 | 91 | 1 |
| M48 | 5 | 77 | 755 | 57 | >3302 | 63 | 4 |
| M48_U1 | 0.65 | 2 | 11 | 5 | 87 | 0.3 | 0.07 |
| M48_U2 | 1.6 | 4 | 98 | 42 | 773 | 3.6 | 0.08 |
| M48_U3 | 2 | 67 | 950 | 364 | >3273 | 29 | 0.13 |
| sCD4 | 20 | 9 | 65 | 15 | >250 | 4 | 0.4 |
| TMC120 | 0.9 | 1.5 | 1.2 | 0.6 | 1.5 | 1.5 | 1.8 |

EC50 (nM)

The antiviral activity is expressed as the 50% Effective Concentration (EC50) (nM).

Values represent the geometric mean of at least 2 individual experiments, in which each condition was tested in 3-fold.

Whether the same CD4 miniproteins displayed similar antiviral activity against other subtype B pseudoviruses which use either CCR5 (Ba-L) or CXCR4 (Mn isolate) as co-receptor, was evaluated next. CD4 miniproteins showed rather similar antiviral activity against R5 viruses Ba-L and SF162, although they (especially M33) were less active against the former (Table IV). For most CD4 miniproteins a better response was obtained against the subtype B, X4 virus MN, indicating maybe a differential interaction with R5 and X4 targeting gp120 envelopes. Remarkably, increased antiviral activity was found for the M48_U1 derivative and that for all the isolates tested.

Since the development of HIV microbicides is especially important for the African continent, in which the HIV/AIDS pandemic is most devastating, HIV microbicides candidates It was newt assessed whether the CD4 miniproteins maintained their antiviral activity in co-cultures of monocyte-derived dendritic cells (MO-DC) and autologous CD4+ T cells, as representative target cells for sexual HIV transmission. Importantly, the replication-competent HIV-1 Ba-L reference strain, was used for these experiments. The virus was shortly pre-incubated with a dilution range of one of the compounds before addition of the MO-DC target cells. The compound remained present during infection and during the first 24 h of the co-culture of the MO-DC with the autologous CD4+ T cells, but was washed away afterwards. The first results, analyzed after 7 days of primary culture, indicated EC50 values in the lower μM range for the compounds evaluated in example 1 (CD4M33, CD4M47 and CD4M48) (Table V) but a lower EC50 in the nM range for M48_U1. This last compound remains the most potent after 14 days of co-culture with an EC50 of 16 nM. In comparison compounds M47 and M48 were less potent, with EC50 values around 1 μM.

TABLE V

Evaluation of the antiviral activity of the M48 derivatives against HIV Ba-L in a replication competent assay with co-cultures of monocyte-derived dendritic cells (MO-DC) and CD4+ T cells.

|  | Primary Culture EC50 (nM) | | Secondary Cult. Cmin (nM) |
| --- | --- | --- | --- |
|  | Day 7 | Day 14 | Day 28 |
| M33 | 1226 | 2142 | >3414 |
| M47 | 149 | 1289 | >3407 |
| M48 | 251 | 926 | 6605 |
| M48_U1 | 0.19 | 16 | 66 |
| M48_U2 | 13 | 53 | 656 |
| M48_U3 | ND | 197 | 6546 |
| TMC120 | 3 | 3 | 100 |

The antiviral activity is expressed as the 50% Effective Concentration (EC50)(nM). Values represent the geometric mean of at least 2 individual experiments, in which each condition was tested in 3-fold In order to detect any latent or subliminal infection of the MO-DC/CD4$^+$ T cell co-cultures, PHA/IL-2 activated PBMC were added at the end of the 14-day primary culture. No viral infection was found in cells which were, during the primary culture, shortly treated with 66 nM of the M48_U1 CD4 miniprotein, indicating protection from replicative infection. Efficiency was similar to N,N-RTI TMC120 reference which was found to be effective at 100 nM in the same condition. CD4 Mimetic Miniproteins Show No Toxicity Towards MO-DC/CD4$^+$ T Cell Co-Cultures or Towards ME-180 Endocervical Cells.

Compounds under development as microbicides should combine a high antiviral activity and a low cytotoxicity. Therefore, it was investigated if a random selection of CD4 miniproteins showed cytotoxic activity to co-cultures of MO-DC and allogeneic CD4$^+$ T cells. Several CD4 miniproteins were analyzed in parallel. After a 5-day treatment, no cellular toxicity was found in comparison to untreated controls for any of the compounds.

Since a microbicide will be applied into the vaginal lumen, also the cytotoxicity towards genital epithelial cells is of importance. The ME-180 cell line as was used as a model for the epithelial cells which line the cervix in vivo. None of the evaluated compounds, including M48, the reference compounds sCD4 showed any cellular toxicity up to a concentration of 10 μg/ml.

EXAMPLE 3

Multimerization of CD4M48

1) Experimental Procedures
1.1) Peptide Synthesis
a) Synthesis of CD4M48-SH and CD4M48-hydrazino.

After peptide elongation as described in example 1, a free thiol or an hydrazino-group were specifically introduced at Lys$_{11}$ by using N-α-Fmoc-N$^ε$-1-(ivDde)-L-lysine (where ivDde is (4,4-dimethyl-2,6-dioxocyclohex-1-ylidene)-3-methylbutyl). ivDde protecting group was removed on the resin by five treatments of 5 min with 2% hydrazine in DMF. S-Acetylthioglycolic acid or tri-Boc-hydrazinoacetic acid were then coupled to the free amine using HOBt/HATU for activation and DIEA as a base. The modified mini-proteins were then cleaved from the resin with reagent K' to give the fully deprotected crude peptides. Oxidation was performed in 0.1 M Tris/HCl buffer, pH 8.0, containing 5.0 mM GSH at a concentration of 0.1 mg/mL for 2 h. After acidification to pH 3.0 with HCl, the folded mini-proteins were then purified by RP-HPLC as described in example 1.

b) Synthesis of Polylysine Constructs for the Formation of Dimers and Tetramers.

The synthesis of polylysine constructs was performed manually on solid phase using Fmoc-PAL-PEG-PS resin and standard Fmoc chemistry (20% piperidine/DMF for Fmoc deprotection, HOBt and HATU for activation, DIEA as a base and DMF as solvent). Fmoc-Lys(Fmoc)-OH was first loaded onto the resin before undergoing Fmoc deprotection. For the dimers, the relevant PEG linkers (3× Fmoc-8-amino-3,6-dioxaoctanoic acid, 1×- or 2×-O—(N-Fmoc-2-aminoethyl)-O'-(2-carboxyethyl)undecaethyleneglycol) were directly coupled to the free amino groups to obtain respectively 30, 50 and 100 Å linkers, then Fmoc-deprotected and coupled to γ-maleimidobutyric acid. For the tetramers, another Fmoc-Lys(Fmoc)-OH was coupled to each free amino group and then deprotected to give four free amines that can further react with the relevant PEG linker and finally with γ-maleimidobutyric acid. All the constructs were then cleaved from the resin by treatment with TFA/Thioanisole/H$_2$O/Anisole (90/5/3/2). After evaporation until dryness and lyophilisation in H$_2$O/CH$_3$CN (5/1), the compounds were characterized by ESI-MS and further used without purification.

c) Ligation Reactions for the Formation of Multimers.

Ligation reactions were performed in a mixture of phosphate buffer, 50 mM, pH 6.6 and CH$_3$CN (1/1). Briefly, 2 mg of CD4M48-SH were dissolved in 5.5 mL of solvent. Then, a solution of a given maleimidopolylysine construct (1 mg/mL) was added stepwise until completion of the reaction which was checked by RP-HPLC. The multimers were then purified on RP-HPLC as described above and characterized by ESI-MS and amino acid analysis.

d) Ligation Reactions for the Formation of CD4M48–Heparin.

5 mg of heparin monoaldehyde were dissolved in 1 mL phosphate buffer, 50 mM, pH 6.6 and reacted with 1 mg CD4M48-hydrazino dissolved in 1 mL H$_2$O/CH$_3$CN (1/1). The completion of the reaction was checked by gel filtration (Superdex 75PC Amersham Biosciences AB Uppsala, 0.1 mL/min, PBS+0.36 M NaCl) coupled to a fluorescence detector (detection of tyrosine: Exc. 274 nm, Em. 303 nm) and the covalent complex was purified in the same way. The pooled fractions were then dialyzed against water at 4° C. and lyophilized.

1.2) Surface Plasmon Resonance Biosensor Measurements.

All experiments were conducted at 25° C. with 20 μL/min flow rate in HBS (50 mM HEPES-buffered saline, 3 mM EDTA, 0.05% Biacore surfactant P20, pH 7.4) with a BIA-CORE 3000 instrument (BIACORE AB).

For binding of multimers to gp120, gp120SF162 was immobilized on a CM5 sensor chip at 9000 RU by the amine coupling kit provided by the manufacturer. Multimers were injected at 125 nM over the surface for 5 min. Since the molecular weights of the injected molecules are different, the resulting curves were also normalized to that of CD4M48 for comparison of the off-rates.

For binding of gp120 in complex with the mini-proteins to CD4i Ab 48d, 48d was immobilized on a CM5 sensor chip at 15000 RU by the amine coupling kit provided by the manufacturer. The different gp120 (SF162, YU2, LAI, HXB2, SF2) were premixed at a final concentration of 50 nM with 3 eq. CD4M48, 3 eq. CD4M48 in presence of 3 eq. LMW heparin or 3 eq. covalent CD4M48–heparin for 60 min before injection at 20 μL/min. All sensorgrams were corrected by substracting the signal from reference flow cell.

1.3) Biological Studies

The experimental procedures are as described in example 1.

2) Results a) Design and Synthesis of Multimers of CD4M48.

Figure 14:
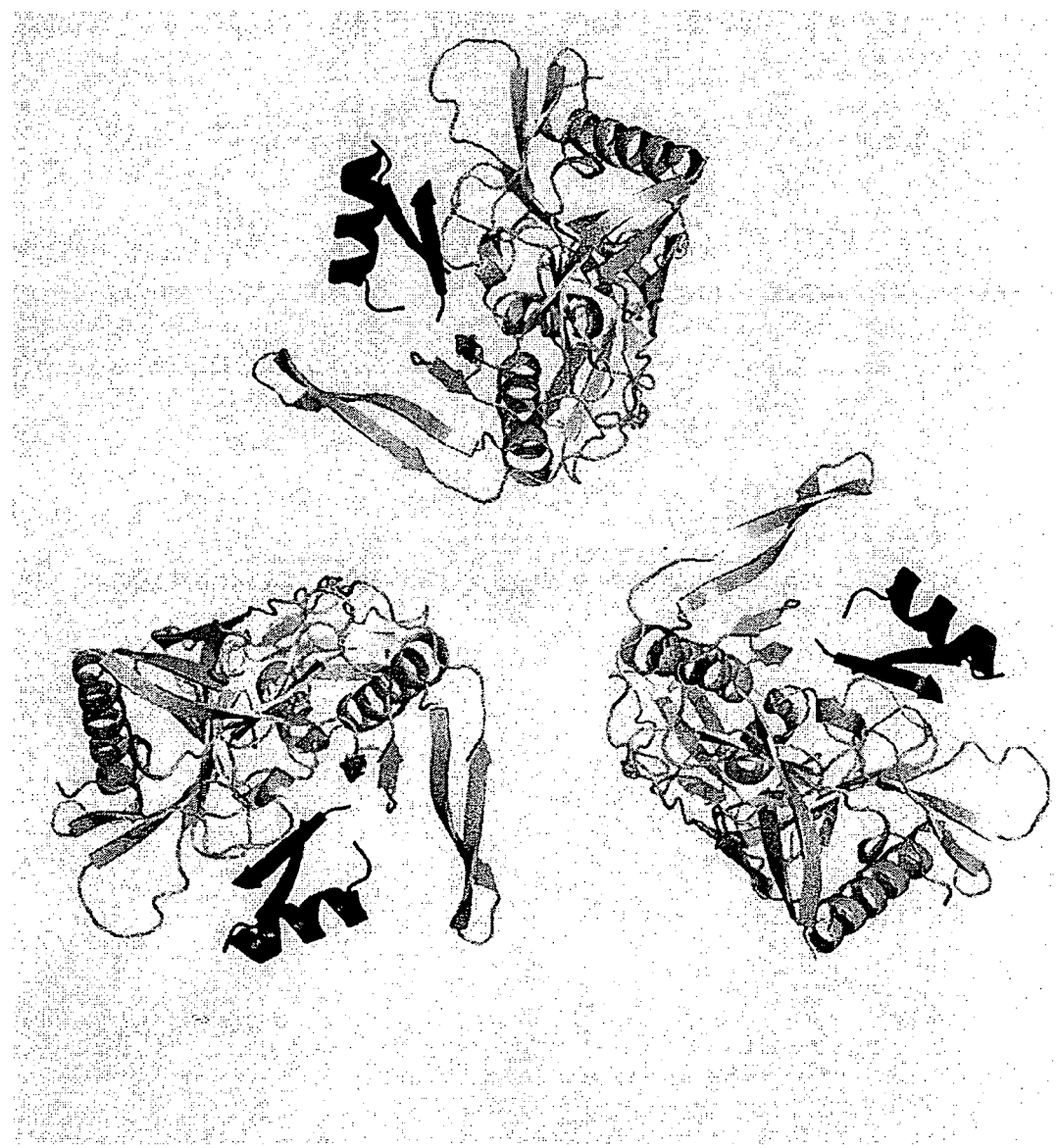
FIG. 14 represents a trimeric model of gp120 in complex with CD4M48. Starting with oligomeric modeling of gp120 depicted in Kwong et al (J. Virol., 2000, 74, 1961-1972), the crystal structure of gp120 in complex with CD4M48 was superposed and fitted to obtain the minimum RMSD between both trimer models.

Based on a model published by Kwong and coworkers in 2000 (Kwong et al., J. Virol., 2000, 74, 1961-1972) and on the crystal structure of CD4M48 in complex with gp120 and Fab 17b (example 1), a trimeric model of gp120 in interaction with three CD4M48 was computed (FIG. 14). In this model, amino groups of Lys11 from one monomer to another (this amino acid is at the opposite face of the binding region and as a result does not interfere with the binding) are distant from 87 Å. Since only core gp120 is represented, it is likely that the distance required to link two sites has to be longer than this value. Dimers as well as tetramers of CD4M48 of different length were hence synthesized (FIG. 15) in order to occupy several CD4 binding sites within a spike or a virion.

These multivalent molecules were based on polylysine constructs. They were synthesized on solid support and reacted with PEGylated linkers to span the distance between two CD4 binding sites and a maleimido group was finally introduced on each arm so that they can be chemoselectively ligated in solution to CD4M48-SH in which was introduced a supplementary thiol. The distance between the center of the trimer and the CD4 binding site Phe-43 cavity was estimated around 50 Å and the distance between two CD4 binding sites around 87 Å. The linear length of the PEGylated linkers was therefore fixed to 30, 50 or 100 Å. The mini-protein was derivatized on Lys-11, in order to introduce a free mercapto group necessary for chemical ligation. Modifications on this amino acid residue, whose side chain points out of the α-helix at the opposite face of CD4 binding site, does not hinder the binding of CD4M48 to gp120. This was checked by introducing several markers, such as biotin or fluorescein, at this position. The labeled molecules were tested in ELISA or by fluorescence polarisation assay without showing any decrease in their inhibitory activity in comparison with CD4M48.

The synthesis and the folding of the mini-protein CD4M48-SH with a supplementary thiol did not bring any difficulty provided that refolding was performed in reduced conditions (5 mM reduced glutathion): folding of the crude mini-protein led to a clear major product with high yield. Chemical ligation was then performed in solution and the resulting dimers (CD4M48D30, CD4M48D50, CD4M48D100) and tetramers (CD4M48T30, CD4M48T50, CD4M48T100) were purified by reversed phase HPLC and characterized by ESI-MS and amino acid quantitative analysis.

b) Design and Synthesis of the Heterobivalent Covalent Complex CD4M48–Heparin.

An hetero-bivalent inhibitor containing the mini-protein CD4M48 covalently linked to heparin was designed. CD4M48 targets the CD4 binding site and like M33, induces the same conformational structural changes in gp120 as CD4. This unmasks the CD4i epitope allowing co-receptor binding, which can be targeted by heparin. For the synthesis of this hetero-construct, the same strategy as for multivalent inhibitors was adopted. Briefly, CD4M48 was derivatized on Lys-11 to introduce a supplementary hydrazino group. The obtained CD4M48-hydrazino was then easily folded and purified by RP-HPLC. It was finally chemoselectively ligated to heparin mono-aldehyde to give the covalent complex, which was purified by gel filtration.

c) Binding Activity of Multimers.

Figure 16:
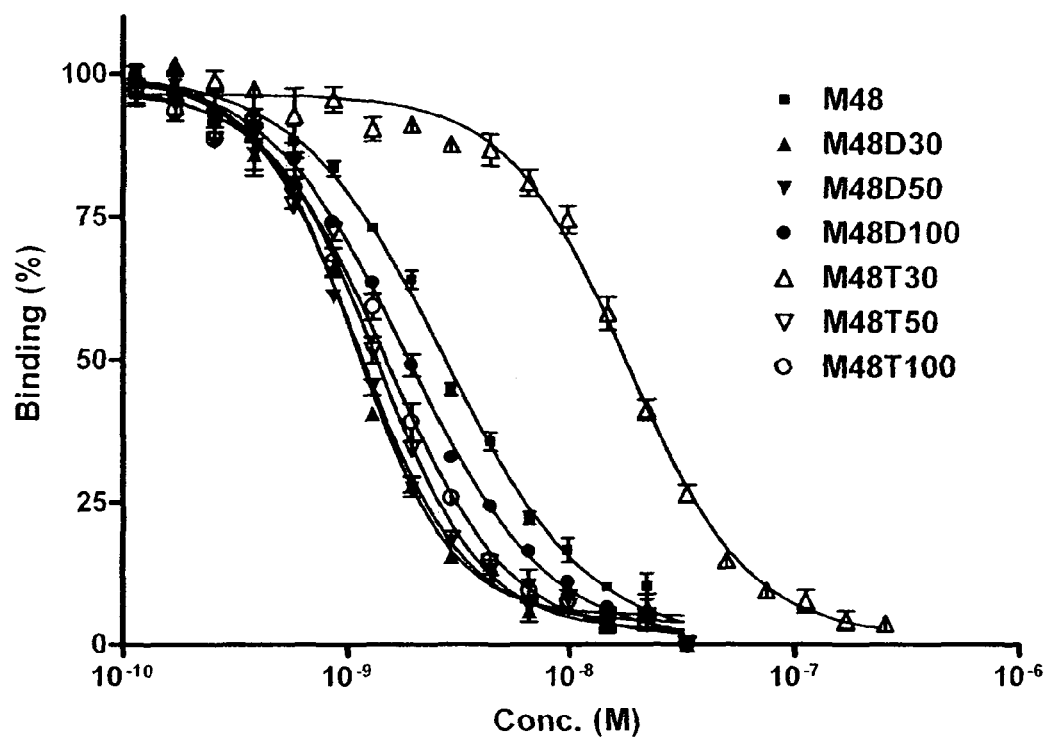
FIG. 16 illustrates the inhibitory activity of dimers and tetramers of CD4M48 obtained by fluorescence polarization. Assays were performed in triplicates using 6 nM gp120SF162, 1 nM fluorescein-CD4M33 and various dilutions of each competitor.
Figure 17:
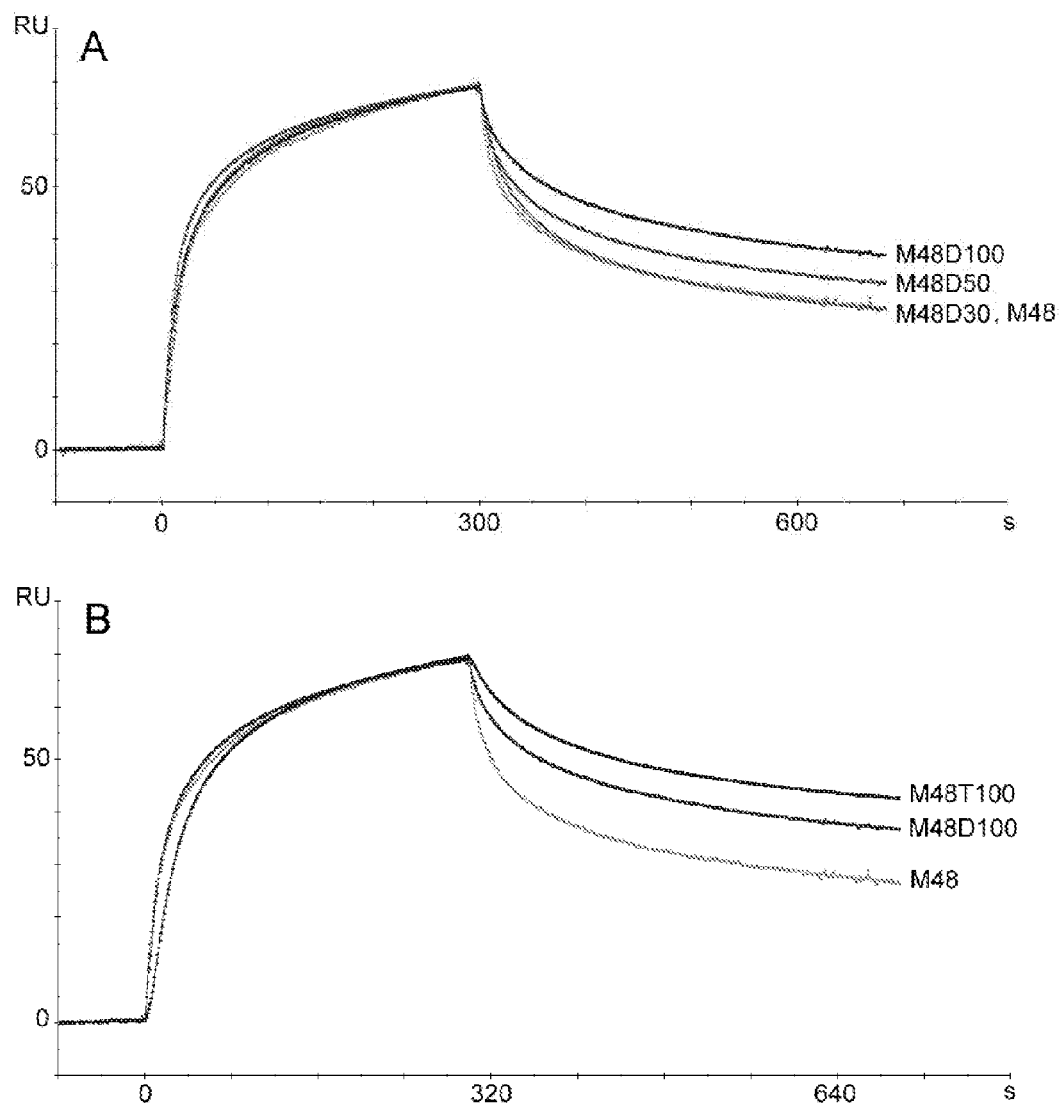
FIG. 17 illustrates the SPR analysis of the binding of CD4M48 monomer, dimers and tetramers to immobilized gp120sf162. gp120SF162 was attached to a CM5 sensor chip by direct amine coupling (9000 RU). 100 μL of monomer, dimers and tetramers were passed over the surface at 20 μL/min after which dissociation of bound inhibitors was monitored for 15 min. After normalization of the curves to that of monomer CD4M48: (A) association and dissociation rates of CD4M48 (M48), CD4M48D30 (M48D30), CD4M48D50 (M48D50) and CD4M48D100 (M48D100) were compared; (B) association and dissociation rates of CD4M48 (M48), CD4M48D100 (M48D100) and CD4M48T100 (M48T100) were compared.

Tested in competition with CD4M33 using fluorescence polarization assays as previously described (Stricher et al., precited), the various constructs, CD4M48, dimers, tetramers except CD4M48T30 all presented roughly comparable affinities to gp120 (FIG. 16). The higher 50% inhibition concentration of this tetramer could be explained by a steric hindrance due to shorter length arms. But to address the binding properties question more accurately in terms of thermodynamics parameters, gp120 was immobilized on a biosensor chip and the association and dissociation phases of dimers and tetramers were monitored. As shown on FIG. 17A, monomer CD4M48 and the corresponding dimers associated in a similar manner with gp120 whereas dissociation of the mini-protein was slowed down when dimerized. This kinetic difference increased with the length of the PEGylated linker where the slowest off-rate was reached for a 100 Å linker. The kinetic properties of the corresponding tetramer CD4M48T100 were also compared to those of dimer CD4M48D100 and monomer CD4M48 (FIG. 17B), indicating a slowed-down dissociation phase with the increase of the number of inhibitor copies involved. The immobilization of monomeric gp120 may of course not perfectly represent the multiple spikes containing trimeric envelope at the surface of a virion. However, this indicates that once an inhibitor dissociates from gp120, it is more likely to rebind another gp120, should it be on the same spike or the same virion, when it is present as a multimer. Besides, the conserved aptitude of multimers to induce the same conformational changes as CD4 in the envelope was confirmed by SPR measurements of the binding of each gp120-multimer complex to CD4-induced antibody 48d.

d) Binding Activity of CD4M48–Heparin.

The ability of the covalent complex CD4M48–heparin to inhibit CD4M33 binding to gp120 was then checked. This inhibitory activity was determined by fluorescence polarization competition assay. CD4M48–heparin was found to inhibit CD4M33 binding in the nanomolar range as demonstrated for CD4M48. The presence of heparin did thus not hinder the binding of the mini-protein to CD4 binding site.

Figure 18:
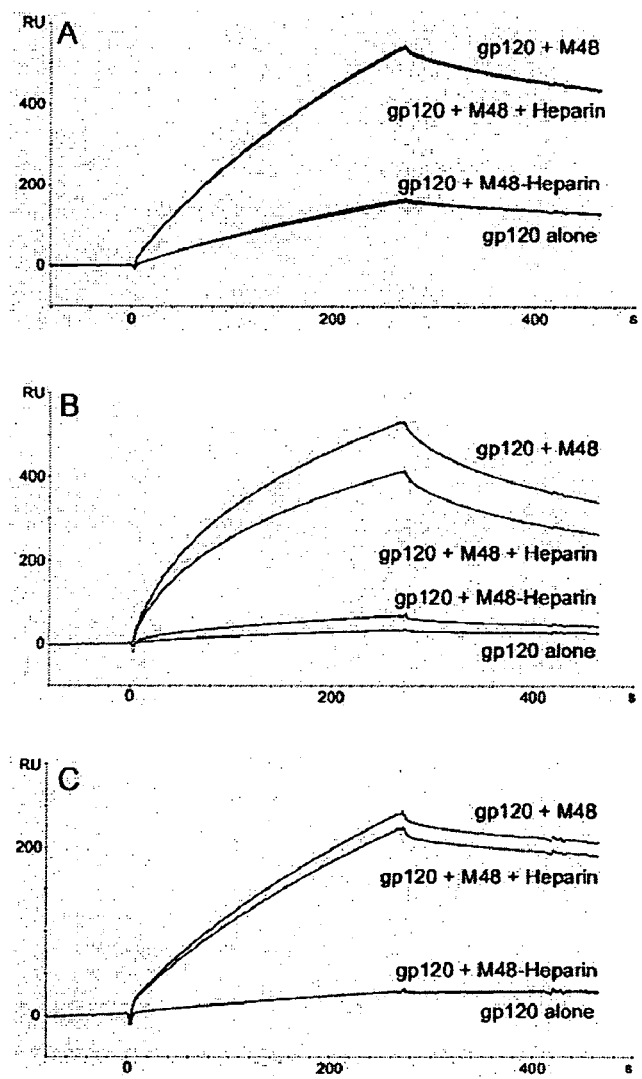
FIG. 18 illustrates the SPR analysis of the binding of CD4M48 monomer and hetero-bivalent CD4M48–heparin in complex with various gp120 to immobilized 48d Ab. CD4i Ab 48d was attached to a CM5 sensor chip by direct amine coupling (15000 RU). 120 μL of 50 nM gp120 preincubated with 3 eq. CD4M48 alone, CD4M48 covalently bound to heparin (noted M48–heparin), CD4M48 in presence of free LMW heparin (1:1) (noted M48+heparin) were then passed over the surface at 20 μL/min after which dissociation was monitored for 15 min. (A) gp120SF162, (B) gp120LAI. (C) gp120YU2.
Figure 19:
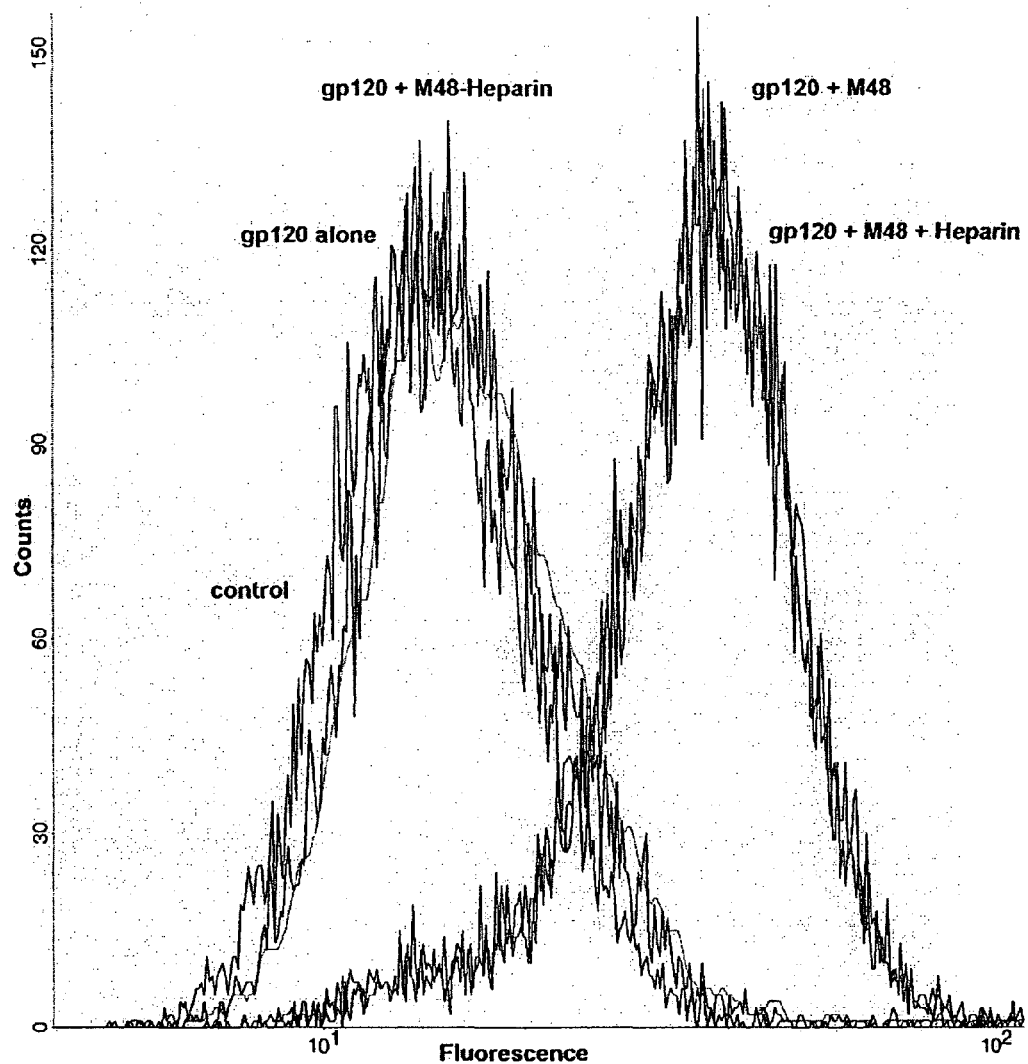
FIG. 19 illustrates the FACS analysis of the binding of gp120SF162 to $CCR5^+$ CHO cells in absence or in presence of CD4M48 monomer or hetero-bivalent CD4M48–heparin. The ability of gp120 in complex with CD4M48 alone, CD4M48 covalently bound to heparin (noted M48–heparin), CD4M48 in presence of free LMW heparin (1:1) (noted M48+heparin) to bind to cellular co-receptor CCR5 was investigated.

Then, to determine whether CD4M48–heparin was also able to inhibit the binding of gp120 to the co-receptor, the binding of different envelope glycoproteins (SF162, YU2, SF2, LAI and HXB2) for CD4i antibody 48d, was measured in the presence of this covalent complex, by surface plasmon resonance technology. This antibody recognizes conserved bridging sheet structures on gp120 that are induced by CD4 or CD4M48 binding and are co-located with a conserved gp120 region that has been shown to be involved in co-receptor binding (Rizutto et al., AIDS Res. Hum. Retrovir., 2000, 16, 741-749). It is therefore a relevant antibody to measure the potential added value brought by heparin to the CD4 mimic. The binding of gp120 to 48d in presence of the covalent complex was compared to that of gp120 with CD4M48 alone or CD4M48 not covalently linked to heparin. Two R5 (SF162 and YU2), two X4 (LAI and HXB2) and one dual-tropic (SF2) envelopes were tested. Some of the results are depicted in FIG. 18. As measured by Biacore, the covalently bound CD4M48–heparin incubated with gp120 was found to inhibit completely the recognition of the complex by CD4i-Ab 48d. The response induced by this complex was indeed found to be brought down to the level of native gp120 (FIG. 18) weakly recognized by CD4i antibodies. This loss of binding activity in comparison with gp120–CD4M48 cannot be imparted to a simple addition of heparin, as the non covalent complex of CD4M48 and heparin in presence of gp120 does not show the same potency (FIG. 18). For R5 envelopes (FIG. 18A), the presence of free heparin does not modify the ability of CD4M48 to induce the conformational change and the binding of gp120 to Ab 48d, whereas, in the case of X4 gp120s (LAI and HXB2), a slight inhibitory activity of the non covalent complex was found (FIG. 18B), consistent with the activity of heparin against X4 viruses described in the literature (Harrop, H. A. and Rider, C. C., Glycobiol., 1998, 8, 131-137; Moulard et al., J. Virol., 2000, 74, 1948-1960). The very good inhibitory results obtained for the covalent complex over the non covalent one are valid for all tested envelopes and suggest a broad inhibitory activity of this molecule independent from co-receptor usage. Although a steric hindrance to the conformational change of the envelope due to the presence of heparin cannot be excluded, it is likely that CD4M48–heparin induces the conformational changes observed for CD4M48 alone. CD4i epitopes important for co-receptor binding should be then unmasked and heparin, thus pre-positioned by its linkage to CD4M48, could then prevent the binding of the co-receptor to these epitopes. Those results were confirmed by FACS analysis where the ability of gp120 in complex with CD4M48–heparin to bind to CCR5+ cells was investigated. As shown on FIG. 19, CD4M48 covalently linked to heparin pre-incubated with gp120SF162 prevents the binding of the complex to CCR5+ cells whereas CD4M48 in presence of free heparin enables the binding of gp120 to CCR5+ cells in a similar extent as CD4M48 alone. As CD4M48–heparin has the same affinity as CD4M48 for the CD4 binding site of gp120, these data indicate a probable masking of the V3 loop preventing the attachment of gp120 to the co-receptor or CD4i antibodies.

e) Virus Inhibition by Multimers and Heterodimers

The ability of multimers and heterodimer CD4M48–heparin to inhibit HIV-1 cell-cell fusion and infection of cells expressing CD4 was then investigated.

For the inhibition of the infection different target cells were tested, as well as different HIV-1 strains. The results are summarized in Tables VI and VII.

TABLE VI

Antiviral activity* of multimers and CD4M48-heparin compared to CD4M48 on PM1 cells

| HIV-1 isolate | BaL(R5) IC$_{50}$ (nM) | 77(X4) IC$_{50}$ (nM) | 6393(R5) IC$_{50}$ (nM) | 714(R5) IC$_{50}$ (nM) |
|---|---|---|---|---|
| CD4M48 | 185 | 250 | 95 | 670 |
| CD4M48D30 | 3.6 | 1.7 | 100 | 50 |
| CD4M48D50 | 2.4 | 0.9 | 55 | 220 |
| CD4M48D100 | 11 | 3 | 11 | 17 |
| CD4M48T30 | 97 | 15.6 | 20 | 390 |
| CD4M48T50 | 310 | 13 | 350 | 680 |
| CD4M48T100 | 45 | <4 | 55 | 360 |
| CD4M48-hep | 850 | <4 | n.d. | n.d. |

*inhibitory concentrations were calculated at day 5

TABLE VII

Antiviral activity* of multimers and M48-heparin compared to CD4M48 and T20 on MT-4 and PBMC cells

| Cell type<br>HIV-1 isolate | MT-4<br>NL4.3 (X4)<br>IC$_{50}$ (nM) | PBMC<br>NL4.3(X4)<br>IC$_{50}$ (nM) |
|---|---|---|
| T20 | 11 | 13 |
| CD4M48 | 2.6 | 0.44 |
| CD4M48D30 | <0.014 | <2.2 |
| CD4M48D50 | 0.053 | 2.6 |
| CD4M48D100 | 1.8 | <1.8 |
| CD4M48T30 | 31 | 37 |
| CD4M48T50 | 31 | <26 |
| CD4M48T100 | 22 | 1.3 |
| CD4M48-hep | 112 | <80 |

*inhibitory concentrations were calculated at day 5 for MT-4 and day 12 for PBMC Almost all multimers showed enhanced inhibitory activity over the monomeric CD4M48 in PM1 cell line (Table VI). The improvement in IC$_{50}$ was particularly striking for the dimers: the concentrations required for 50% virus inhibition were from 1 log to more than 2 log lower than those required for CD4M48, independently from the isolate tropism. The best results were obtained against BaL and 77 viruses where the inhibitory activity could be brought down to low nanomolar range (Table VI). Likewise, in MT-4 cell line, dimers were demonstrated to be far more potent than the corresponding tetramers and than CD4M48 against NL4.3 virus (Table VII). In this assay, the IC$_{50}$ of CD4M48D30 was reduced to an outstanding picomolar value, confirming the remarkable activity of these dimeric inhibitors. In PM1 cell line, CD4M48D100 seemed to be the broadest inhibitor, whereas in MT-4, CD4M48D30 appeared to be the most efficient. Hence, no conclusion about the right length of the PEGylated linker used to build the multimers could be drawn. This may suggest that two "PEG arms" of 30 Å should be enough in this construction to span the distance between two CD4 binding sites and that longer ones could just bring supplementary flexibility. It is also likely that on a multimer, not all molecules of CD4M48 bind simultaneously to several gp120s. Multimerization increases the local concentration in inhibitor present around a spike or a virion which simply enables those molecules to better compete with cellular CD4 than monomeric ones. The enhanced ability of the multimers to block the entry of the virus may be explained by their bi-functionality as Env has been shown to tolerate the presence of defective subunits and to need inhibition of several members of the oligomer to be inactivated. The increased potency of the dimers compared to that of the tetramers may indicate that inhibition of two CD4 binding sites might be enough to inactivate a trimeric spike.

Heterodimer CD4M48–heparin was also tested in PM1 cell line against BaL and 77 and in MT-4 cell line against NL4.3. Data indicate various effects due to the presence of heparin, depending on the strain and on the assay. The covalent linkage of CD4M48 with heparin did not bring any improvement in activity for BaL virus in PM1 and NL4.3 virus in MT-4. On the contrary, a strong improvement of the IC$_{50}$ for virus 77 was observed (Table VI). CD4M48–heparin inhibited infection by this X4 strain in PM1 with an IC$_{50}$ lower than 4 nM, while the CD4M48 concentrations necessary to obtain 50% virus inhibition was only 250 nM. This confirms the ability of heparin to better bind viruses from X4 tropism.

The invention claimed is:

1. An isolated peptide, characterized in that it comprises the following sequence (I):
TPA-Asn-Leu-His-Phe-Cys-Gln-Leu-Xaa$^a$-Cys-Lys-Ser-Leu-Gly-Leu-Leu-Gly-Arg-Cys-Xaa$^b$-Xaa$^c$-Xaa$^d$-Xaa$^e$-Cys-Ala-Cys-Val-NH$_2$ (SEQ ID NO: 2), wherein TPA represents thiopropionic acid, Xaa$^a$ represents Arg or Lys, Xaa$^b$ represents Ala or Arg, Xaa$^c$ represents a D-amino acid, Xaa$^d$ represents Thr, Ser or Asn, and Xaa$^e$ represents phenylalanine or a phenylalanine derivative having the structure (II):

$H_2N$ COOH
[structure with benzene ring] A—(B)$n$—R, where A is absent or represents S, O, NH or CH$_2$, B is absent or represents a C$_1$ to C$_6$ branched or straight-chain alkyl, and R represents a C$_3$ to C$_6$ alkyl, heteroalkyl, cycloalkyl, heterocycloalkyl, cycloalkenyl, cycloheterocycloalkenyl, aryl, or heteroaryl.

2. The peptide according to claim 1, characterized in that Xaa$^a$ is lysine.

3. The peptide according to claim 1, characterized in that Xaa$^b$ is alanine.

4. The peptide according to claim 1, characterized in that Xaa$^c$ is (D)proline.

5. The peptide according to claim 1, characterized in that Xaa$^d$ is threonine.

6. The peptide according to claim 1, characterized in that it comprises a phenylalanine derivative of the structure (II) which is a biphenylalanine.

7. The peptide according to claim 1, characterized in that it comprises a phenylalanine derivative of the structure (II) wherein B represents a C$_1$ to C$_3$ straight-chain alkyl.

8. The peptide according to claim 7, characterized in that the phenylalanine derivative of the structure (II) is selected from the group consisting of: para-cyclo-hexylmethoxyphenylalanine and para-cyclo-pentylethoxyphenylalanine.

9. The peptide according to claim 1, characterized in that it has a sequence seected from the group consisting of SEQ ID NOs: 3 to 6.

10. The peptide according to claim 1, characterized in that the Lys residue in position 9 or 11 is modified by a thiol, an hydrazino group, a maleimido group, or a N-hydroxysuccinimidyl ester.

11. The peptide according to claim 1, characterized in that it is a monomer.

12. The peptide according to claim 1, characterized in that it is a multimer wherein each peptide is linked to the other by a spacer of a length which is appropriate for binding of the peptides to the CD4 binding sites on the trimeric HIV gp120 complex.

13. The peptide according to claim 12, characterized in that it is a dimer.

14. The peptide according to claim 12, characterized in that the length of the spacer is from 30 Å to about 100 Å.

15. The peptide according to claim 12, characterized in that the spacer is covalently linked to a modified lysine residue in position 9 or 11 of the peptide, as defined in claim 10.

16. The peptide according to claim 1, characterized in that it is labeled with an appropriate probe.

17. A multivalent antiviral compound, characterized in that it comprises at least one peptide as defined in claim 1, linked to an HIV entry inhibitor selected from the group consisting of: co-receptor-gp120 binding inhibitors and viral-cell fusion inhibitors.

18. The multivalent antiviral compound according to claim 17, characterized in that the peptide is linked to a polyanion.

19. The multivalent compound according to claim 18, characterized in that the polyanion is heparin or heparin sulfate.

20. An antiviral composition, characterized in that it comprises a peptide according to claim 1, in an acceptable carrier.

21. The composition according to claim 20, characterized in that it comprises at least one additional anti-HIV drug.

22. An immunogenic composition, characterized in that it comprises a complex of a peptide according to claim 1 and an HIV Env polypeptide, in an acceptable carrier.

23. A method for the preparation of a diagnostic reagent for the detection of HIV infection, comprising labeling a peptide according to claim 1 with a detectable probe.

24. A method of producing HIV neutralizing antibodies, comprising the steps of:
administering a complex as defined in claim 22 to a subject, under conditions that allow the production of antibodies, and
recovering antibodies from said subject.

25. A method for the purification of a HIV Env protein, comprising:
contacting a sample containing a HIV Env protein with a peptide according to claim 1;
allowing a complex to form between the HIV Env protein and the peptide; and
purifying the complex.

26. A method for the detection of a HIV Env protein, comprising:
- contacting a sample containing a HIV Env protein with a peptide according to claim 1;
- allowing a complex to form between the HIV Env protein and the peptide; and
- detecting the complex.

27. A method for screening molecules which inhibit the interaction of gp120 or one of its analogues with a CD4 molecule or one of its mimics, comprising:
- contacting gp120 or one of its analogues with a peptide according to claim 1 and a molecule to be screened, wherein the peptide comprises a detectable probe; and
- detecting competition between the peptide and the molecule for binding to gp120 or one of its analogues.

28. An antiviral composition, characterized in that it comprises a peptide according to claim 17 in an acceptable carrier.

* * * * *

UNITED STATES PATENT AND TRADEMARK OFFICE
CERTIFICATE OF CORRECTION

PATENT NO. : 8,354,498 B2  
APPLICATION NO. : 12/304485  
DATED : January 15, 2013  
INVENTOR(S) : Claudio Vita et al.

Page 1 of 1

It is certified that error appears in the above-identified patent and that said Letters Patent is hereby corrected as shown below:

In the Claims:

In Claim 9, at Column 39, line 62, delete "seected" and replace it with --selected--.

Signed and Sealed this  
Twenty-first Day of May, 2013

Teresa Stanek Rea  
*Acting Director of the United States Patent and Trademark Office*

SEQUENCE LISTING

<160> NUMBER OF SEQ ID NOS: 6

<210> SEQ ID NO 1
<211> LENGTH: 27
<212> TYPE: PRT
<213> ORGANISM: artificial sequence
<220> FEATURE:
<223> OTHER INFORMATION: CD4 mimic peptide
<220> FEATURE:
<221> NAME/KEY: MOD_RES
<222> LOCATION: (1)..(1)
<223> OTHER INFORMATION: thiopropionic acid
<220> FEATURE:
<221> NAME/KEY: MOD_RES
<222> LOCATION: (23)..(23)
<223> OTHER INFORMATION: bi-phenylalanine

<400> SEQUENCE: 1

Xaa Asn Leu His Phe Cys Gln Leu Arg Cys Lys Ser Leu Gly Leu Leu
 1               5                  10                  15

Gly Lys Cys Ala Gly Ser Xaa Cys Ala Cys Val
            20                  25

<210> SEQ ID NO 2
<211> LENGTH: 27
<212> TYPE: PRT
<213> ORGANISM: artificial sequence
<220> FEATURE:
<223> OTHER INFORMATION: CD4 mimic peptide
<220> FEATURE:
<221> NAME/KEY: MOD_RES
<222> LOCATION: (1)..(1)
<223> OTHER INFORMATION: thioproponic acid
<220> FEATURE:
<221> NAME/KEY: VARIANT
<222> LOCATION: (9)..(9)
<223> OTHER INFORMATION: Arginine or Lysine
<220> FEATURE:
<221> NAME/KEY: VARIANT
<222> LOCATION: (20)..(20)
<223> OTHER INFORMATION: Alanine or Arginine
<220> FEATURE:
<221> NAME/KEY: VARIANT
<222> LOCATION: (21)..(21)
<223> OTHER INFORMATION: D-amino acid
<220> FEATURE:
<221> NAME/KEY: VARIANT
<222> LOCATION: (22)..(22)
<223> OTHER INFORMATION: Threonine, Serine, or Asparagine
<220> FEATURE:
<221> NAME/KEY: VARIANT
<222> LOCATION: (23)..(23)
<223> OTHER INFORMATION: phenylalanine or bi-cyclic phenylalanine
      derivative of the structure (II)

<400> SEQUENCE: 2

Xaa Asn Leu His Phe Cys Gln Leu Xaa Cys Lys Ser Leu Gly Leu Leu
 1               5                  10                  15

Gly Arg Cys Xaa Xaa Xaa Cys Ala Cys Val
            20                  25

<210> SEQ ID NO 3
<211> LENGTH: 27
<212> TYPE: PRT
<213> ORGANISM: artificial sequence
<220> FEATURE:
<223> OTHER INFORMATION: CD4 mimic peptide
<220> FEATURE:
<221> NAME/KEY: MOD_RES
<222> LOCATION: (1)..(1)
<223> OTHER INFORMATION: Thiopropionic acid

```
<220> FEATURE:
<221> NAME/KEY: MOD_RES
<222> LOCATION: (21)..(21)
<223> OTHER INFORMATION: D-proline
<220> FEATURE:
<221> NAME/KEY: MOD_RES
<222> LOCATION: (23)..(23)
<223> OTHER INFORMATION: bi-phenylalanine

<400> SEQUENCE: 3

Xaa Asn Leu His Phe Cys Gln Leu Arg Cys Lys Ser Leu Gly Leu Leu
1               5                   10                  15

Gly Arg Cys Ala Xaa Thr Xaa Cys Ala Cys Val
            20                  25

<210> SEQ ID NO 4
<211> LENGTH: 27
<212> TYPE: PRT
<213> ORGANISM: artificial sequence
<220> FEATURE:
<223> OTHER INFORMATION: CD4 mimic peptide
<220> FEATURE:
<221> NAME/KEY: MOD_RES
<222> LOCATION: (1)..(1)
<223> OTHER INFORMATION: thiopropionic acid
<220> FEATURE:
<221> NAME/KEY: MOD_RES
<222> LOCATION: (21)..(21)
<223> OTHER INFORMATION: D-proline

<400> SEQUENCE: 4

Xaa Asn Leu His Phe Cys Gln Leu Arg Cys Lys Ser Leu Gly Leu Leu
1               5                   10                  15

Gly Arg Cys Ala Xaa Thr Phe Cys Ala Cys Val
            20                  25

<210> SEQ ID NO 5
<211> LENGTH: 27
<212> TYPE: PRT
<213> ORGANISM: artificial sequence
<220> FEATURE:
<223> OTHER INFORMATION: CD4 mimic peptide
<220> FEATURE:
<221> NAME/KEY: MOD_RES
<222> LOCATION: (1)..(1)
<223> OTHER INFORMATION: thiopropionic acid
<220> FEATURE:
<221> NAME/KEY: MOD_RES
<222> LOCATION: (21)..(21)
<223> OTHER INFORMATION: D-proline
<220> FEATURE:
<221> NAME/KEY: MOD_RES
<222> LOCATION: (23)..(23)
<223> OTHER INFORMATION: para-cyclo-hexylmethoxyphenylalanine

<400> SEQUENCE: 5

Xaa Asn Leu His Phe Cys Gln Leu Arg Cys Lys Ser Leu Gly Leu Leu
1               5                   10                  15

Gly Arg Cys Ala Xaa Thr Xaa Cys Ala Cys Val
            20                  25

<210> SEQ ID NO 6
<211> LENGTH: 27
<212> TYPE: PRT
<213> ORGANISM: artificial sequence
<220> FEATURE:
<223> OTHER INFORMATION: CD4 mimic peptide
<220> FEATURE:
<221> NAME/KEY: MOD_RES
<222> LOCATION: (1)..(1)
<223> OTHER INFORMATION: Thiopropionic acid
```

```
<220> FEATURE:
<221> NAME/KEY: MOD_RES
<222> LOCATION: (21)..(21)
<223> OTHER INFORMATION: D-proline
<220> FEATURE:
<221> NAME/KEY: MOD_RES
<222> LOCATION: (23)..(23)
<223> OTHER INFORMATION: para-cyclo-pentylethoxyphenylalanine

<400> SEQUENCE: 6

Xaa Asn Leu His Phe Cys Gln Leu Arg Cys Lys Ser Leu Gly Leu Leu
1               5                   10                  15

Gly Arg Cys Ala Xaa Thr Xaa Cys Ala Cys Val
            20              25
```